United States Patent
Stenzler et al.

(10) Patent No.: US 7,122,018 B2
(45) Date of Patent: Oct. 17, 2006

(54) DEVICE AND METHOD FOR TREATMENT OF WOUNDS WITH NITRIC OXIDE

(75) Inventors: Alex Stenzler, Long Beach, CA (US); Chris C Miller, North Vancouver (CA)

(73) Assignees: Sensormedics Corporation, Yorba Linda, CA (US); Pulmonox Technologies Corporation, Edmonton (CA)

(*) Notice: Subject to any disclaimer, the term of this patent is extended or adjusted under 35 U.S.C. 154(b) by 0 days.

(21) Appl. No.: 11/021,109

(22) Filed: Dec. 23, 2004

(65) Prior Publication Data

US 2005/0191372 A1    Sep. 1, 2005

Related U.S. Application Data

(63) Continuation-in-part of application No. 10/944,479, filed on Sep. 17, 2004, and a continuation-in-part of application No. 10/615,546, filed on Jul. 8, 2003, said application No. 10/944,479 is a continuation of application No. 10/172,270, filed on Jun. 14, 2002, now Pat. No. 6,793,644, which is a continuation of application No. 09/749,022, filed on Dec. 26, 2000, now Pat. No. 6,432,077, said application No. 10/615,546.

(60) Provisional application No. 60/431,876, filed on Dec. 9, 2002, provisional application No. 60/409,400, filed on Sep. 10, 2002, provisional application No. 60/394,690, filed on Jul. 9, 2002.

(51) Int. Cl.
*A61M 37/00* (2006.01)
*A61M 1/00* (2006.01)
*A01N 59/02* (2006.01)

(52) U.S. Cl. ............ 604/23; 604/290; 604/289; 604/540; 604/543; 424/718

(58) Field of Classification Search .............. 604/23, 604/290, 25, 540, 543, 289; 424/718; 514/579, 514/645; 435/7.1, 5, 6; 436/518, 534, 528, 436/501
See application file for complete search history.

(56) References Cited

U.S. PATENT DOCUMENTS

| | | | |
|---|---|---|---|
| 5,154,697 A | 10/1992 | Loori | 604/23 |
| 5,514,204 A * | 5/1996 | Sheu et al. | 95/92 |
| 5,519,020 A * | 5/1996 | Smith et al. | 424/718 |
| 5,688,236 A | 11/1997 | Gragg | 604/23 |
| 6,060,020 A | 5/2000 | Piuk et al. | 422/33 |

(Continued)

FOREIGN PATENT DOCUMENTS

WO    WO 00/07653    2/2000

*Primary Examiner*—Jacqueline F. Stephens
(74) *Attorney, Agent, or Firm*—Sidley Austin LLP

(57) ABSTRACT

Topical exposure of nitric oxide gas to wounds such as chronic non-healing wounds may be beneficial in promoting healing and preparing the wound bed for further treatment and recovery. Nitric oxide gas may be used to reduce the microbial infection, manage exudates secretion by reducing inflammation, upregulate expression of endogenous collagenase to locally debride the wound, and regulate the formation of collagen. High concentration of nitric oxide ranging from 160–400 ppm may be used without inducing toxicity in the healthy cells around a wound site. Exposure to the high concentration for a first treatment period reduces the microbial burden and inflammation, and increases collagenase expression to debride necrotic tissue at the wound site. After a first treatment period, a second treatment period at a lower concentration of nitric oxide, preferably ranging from 5–20 ppm may be used to restore the balance of nitric oxide and induce collagen expression aiding in the wound closure.

15 Claims, 26 Drawing Sheets

U.S. PATENT DOCUMENTS

| | | | |
|---|---|---|---|
| 6,071,254 A | 6/2000 | Augustine | 602/2 |
| 6,073,627 A | 6/2000 | Sunnen | 128/202.25 |
| 6,083,209 A | 7/2000 | Marasco, Jr. | 604/290 |
| 6,103,275 A * | 8/2000 | Seitz et al. | 424/718 |
| 6,110,895 A * | 8/2000 | Rodgers et al. | 514/15 |
| 6,160,021 A * | 12/2000 | Lerner et al. | 514/645 |
| 6,190,704 B1 | 2/2001 | Murrell | 424/718 |
| 6,747,062 B1 | 6/2004 | Murrell | 514/565 |
| 6,793,644 B1 * | 9/2004 | Stenzler | 604/23 |
| 2002/0138051 A1 * | 9/2002 | Hole et al. | 604/305 |
| 2002/0155164 A1 * | 10/2002 | Figley et al. | 424/600 |
| 2003/0165578 A1 | 9/2003 | Murrell | 424/718 |
| 2004/0043026 A1 * | 3/2004 | Tuan et al. | 424/146.1 |

* cited by examiner

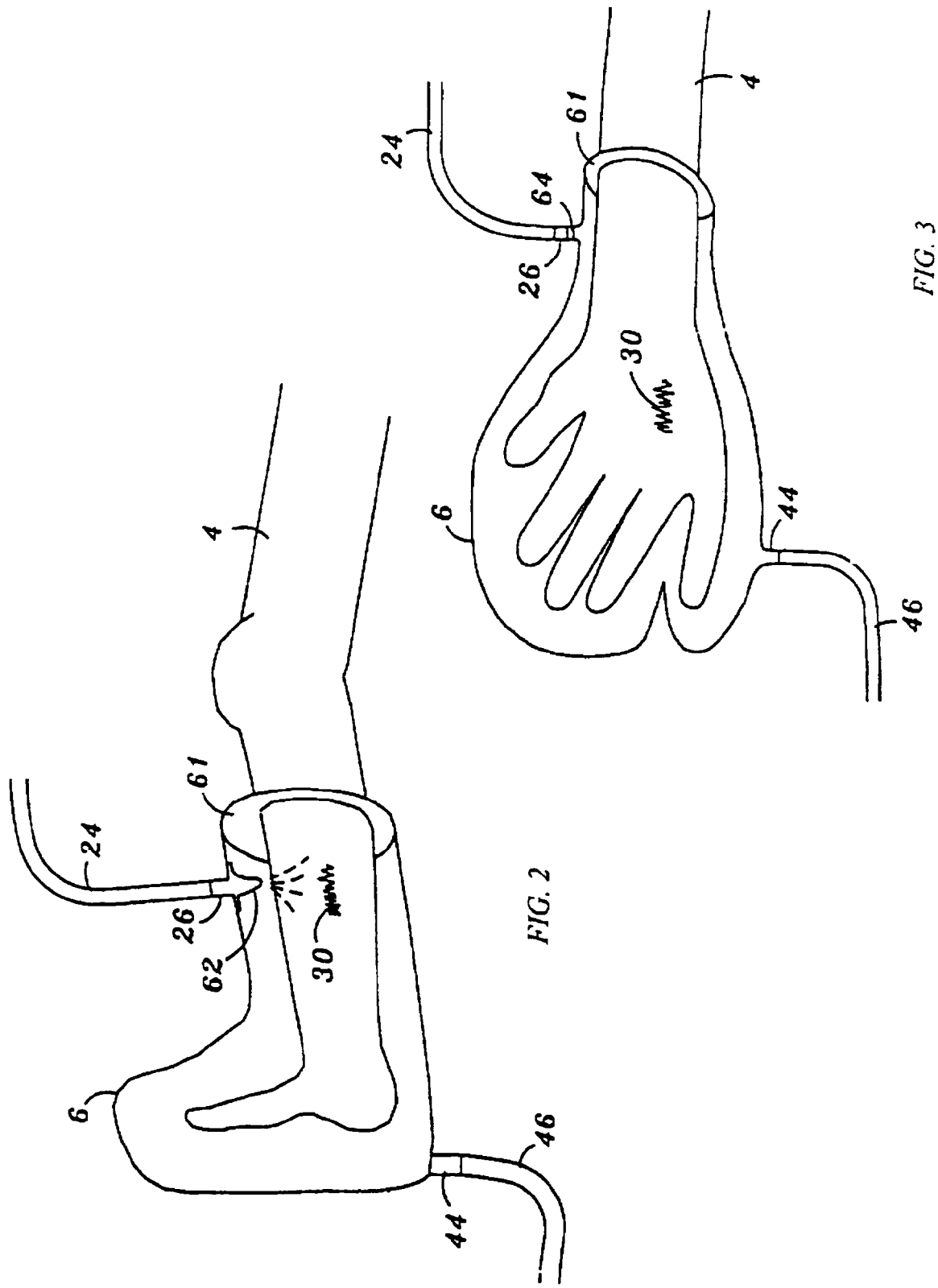

Effect of 200 ppm gNO on *S. aureus* (ATCC#25923)

Effect of 200 ppm gNO on *P. aeruginosa* (ATCC#27853)

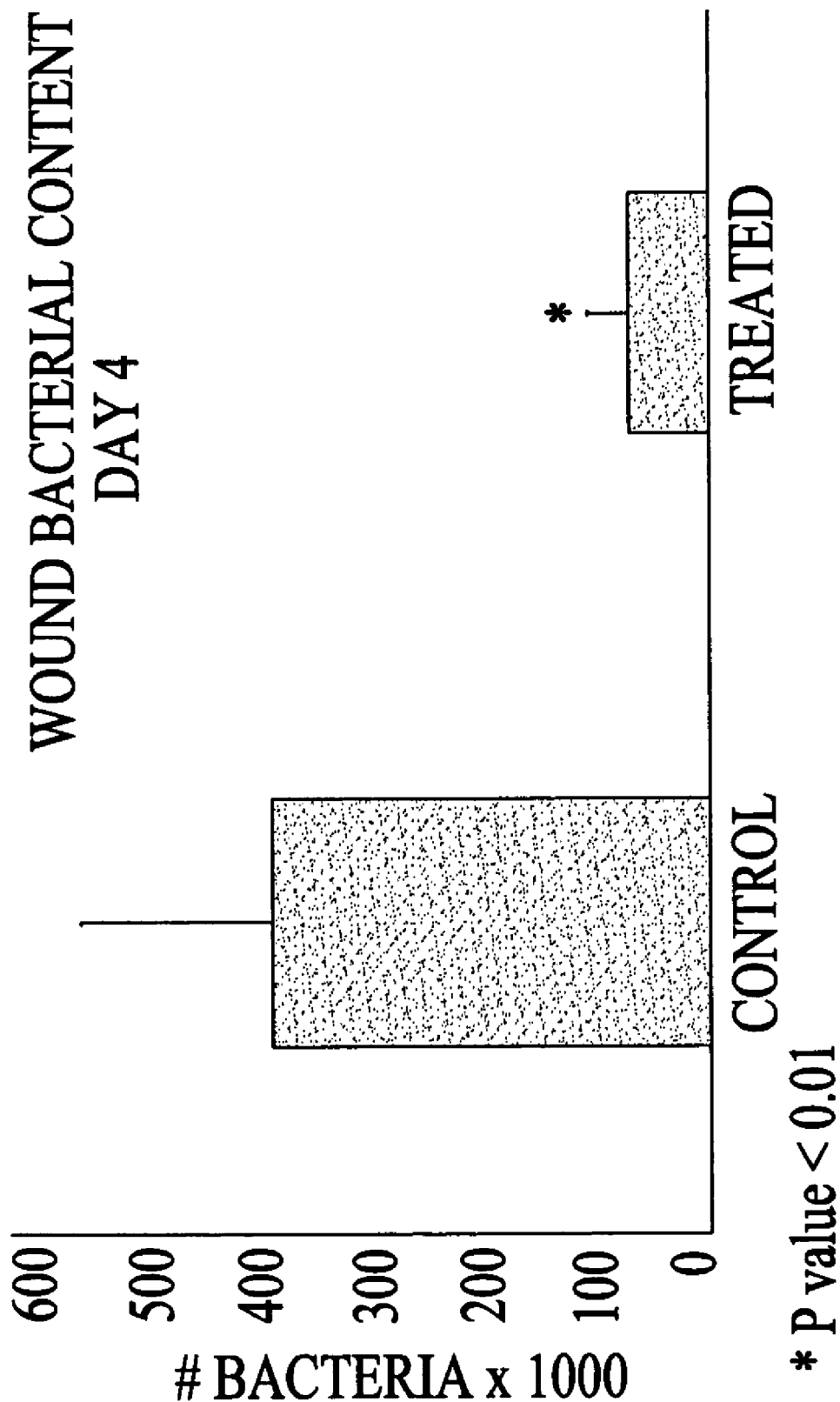

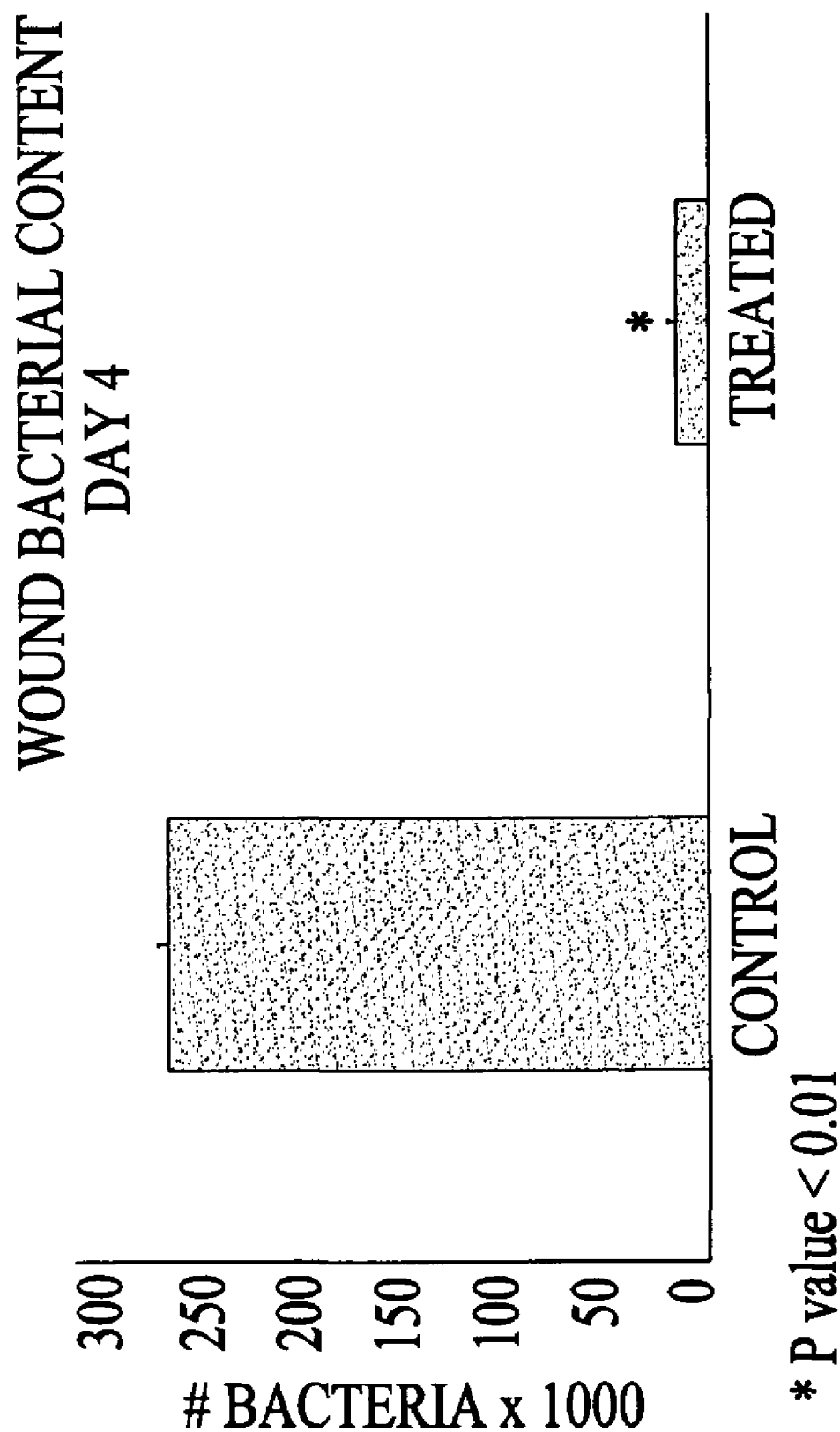

FIG. 14
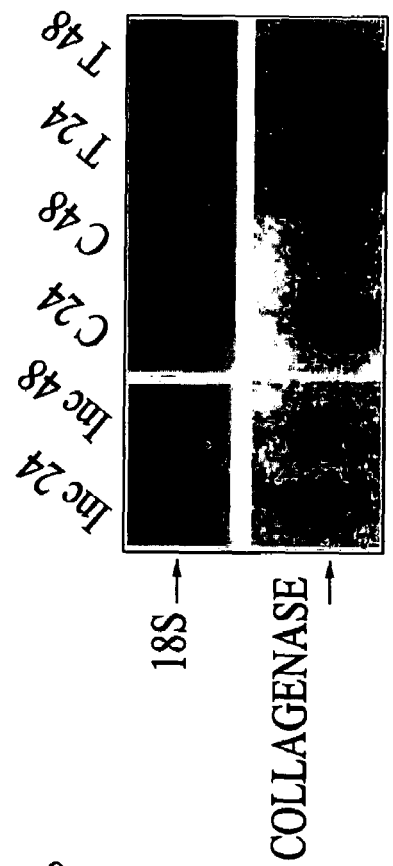
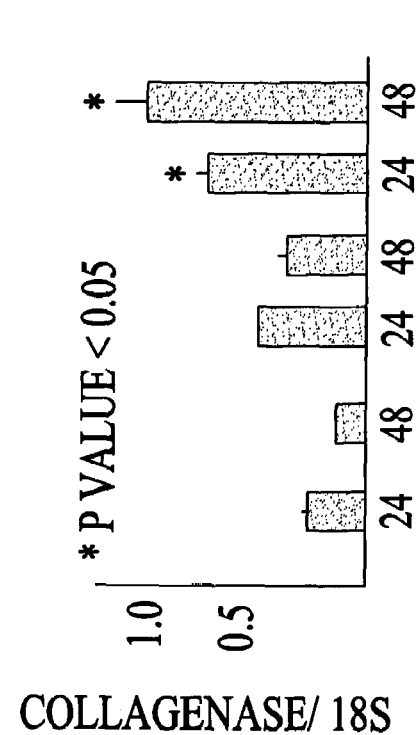
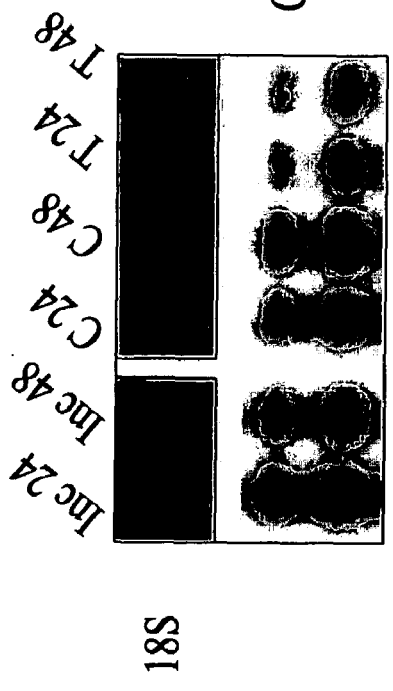
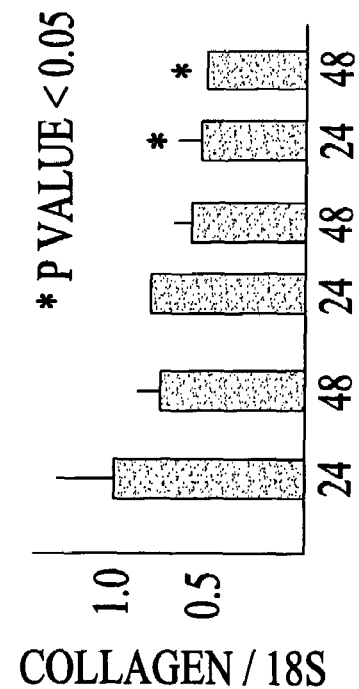

FIG. 15
(b)
(a)

NUMBER OF MIGRATED FIBROBLASTS

3D FIBROBLAST PROLIFERATION

COLLAGEN EXPRESSION AT 5 ppm NO

FIBROBLASTS 5 ppm NO

DEVICE AND METHOD FOR TREATMENT OF WOUNDS WITH NITRIC OXIDE

This application is a continuation in part of U.S. application Ser. No. 10/944,479, filed Sep. 17, 2004, and U.S. application Ser. No. 10/615,546, filed Jul. 8, 2003.

U.S. application Ser. No. 10/944,479 is a continuation of U.S. application Ser. No. 10/172,270, filed Jun. 14, 2002 and issued as U.S. Pat. No. 6,793,644, which in turn is a continuation of U.S. application Ser. No. 09/749,022, filed on Dec. 26, 2000 and issued as U.S. Pat. No. 6,432,077.

U.S. application Ser. No. 10/615,546 claims priority to U.S. Provisional Application Nos. 60/431,876, filed Dec. 9, 2002, 60/409,400, filed Sep. 10, 2002, and 60/394,690, filed Jul. 9, 2002.

The above patents and patent applications are incorporated by reference as if set forth fully herein.

FIELD OF THE INVENTION

The field of the invention relates to devices and methods for treating wounds and infections, and more specifically, the treatment of wounds and infections with nitric oxide.

BACKGROUND OF THE INVENTION

The treatment of infected surface or subsurface lesions in patients has typically involved the topical or systemic administration of anti-infective agents to a patient. Antibiotics are one such class of anti-infective agents that are commonly used to treat an infected abscess, lesion, wound, or the like. Unfortunately, an increasingly number of infective agents such as bacteria have become resistant to conventional antibiotic therapy. Indeed, the increased use of antibiotics by the medical community has led to a commensurate increase in resistant strains of bacteria that do not respond to traditional or even newly developed anti-bacterial agents.

For example, *Staphylococci* are known to be significant pathogens that cause severe infections in humans, including endocarditis, pneumonia, sepsis and toxic shock. Methicillin resistant *S. aureus* (MRSA) is now one of the most common causes of nosocomial infections worldwide, causing up to 89.5% of all staphylococci infection. Community outbreaks of MRSA have also become increasingly frequent. The main treatment for these infections is the administration of glycopeptides (Vancomycin and Teicoplanin). MRSA have been reported for two decades, but emergence of glycopeptide-resistance in *S. aureus*—namely glycopeptide intermediate (GISA) has been reported only since 1997.[22] The glycopeptides are given only parenterally, and have many toxic side effects. The recent isolation of the first clinical Vancomycin-resistant strains (VRSA) from a patient in USA has heightened the importance and urgency of developing new agents. Even when new anti-infective agents are developed, these agents are extremely expensive and available only to a limited patient population.

*P. aeruginosa* is another problematic pathogen that is difficult to treat because of its resistance to antibiotics. It is often acquired in the hospital and causes severe respiratory tract infections. *P. aeruginosa* is also associated with high mortality in patients with cystic fibrosis, severe burns, and in AIDS patients who are immunosuppressed. The clinical problems associated with this pathogen are many, as it is notorious for its resistance to antibiotics due to the permeability barrier afforded by its outer membrane lipopolysaccharide (LPS). The tendency of *P. aeruginosa* to colonize surfaces in a biofilm phenotype makes the cells impervious to therapeutic concentrations of antibiotics.

Another problem with conventional anti-infective agents is that some patients are allergic to the very compounds necessary to their treat their infection. For these patients, only few drugs might be available to treat the infection. If the patient is infected with a strain of bacteria that does not respond well to substitute therapies, the patient's life can be in danger.

A separate problem related to conventional treatment of surface or subsurface infections is that the infective agent interferes with the circulation of blood within the infected region. It is sometimes the case that the infective agent causes constriction of the capillaries or other small blood vessels in the infected region which reduces bloodflow. When bloodflow is reduced, a lower level of anti-infective agent can be delivered to the infected region. In addition, the infection can take a much longer time to heal when bloodflow is restricted to the infected area. This increases the total amount of drug that must be administered to the patient, thereby increasing the cost of using such drugs. Topical agents may sometimes be applied over the infected region. However, topical anti-infective agents do not penetrate deep within the skin where a significant portion of the bacteria often reside. Topical treatments of anti-infective agents are often less effective at eliminating infection than systemic administration (i.e., oral administration) of an anti-infective pharmaceutical.

In addition, despite recent advances in chronic wound care, many lower extremity ulcers do not heal. Chronic ulcers of the lower extremities are a significant public health problem. Besides the large financial burden placed on the health care system for their treatment, they cause a heavy toll in human suffering. As the population ages and with the current obesity crisis in North America, venous, diabetic, and pressure ulcers are likely to become ever more common. Approximately 4 million (1% of population) people in the United States develop chronic lower leg ulcers, the majority classified as diabetic or venous leg ulcers, and this number can climb to 4%–5% in older (>80 years of age) patients.

Aside from infection, a variety of factors can potentially influence wound healing of chronic ulcers. These include excessive exudate, necrotic tissue, poor tissue handling, and impaired tissue perfusion, as well as from clinical conditions such as advanced age, diabetes, and steroid administration.

Exudate is a clear, straw colored liquid produced by the body in response to tissue damage. Although exudate is primarily water, it also contains cellular materials, antibodies, nutrients and oxygen. In the immediate response to an injury, exudate is produced by the body to flush away any foreign materials from the site. It then is the carrier for polymorphs and monocytes so that they may ingest bacteria and other debris. Exudate also enables the movement of these phagocytic cells within the wound to help clean it as well as enables the migration of epithelial cells across the wound surface.

While exudate is an important component of wound healing, too much of it in response to chronic inflammation can worsen a wound as the enzymes in the fluid can attack healthy tissues. This may exacerbate the failure of the wound to close as well as place additional psychological pressure on the patient. Chronic wounds frequently have excessive exudate, usually associated with a chronic infection and/or biofilm that has upregulated the inflammatory cells of the body. This may be a local response or may include a systemic increase in inflammatory markers and circulating cytokines.

Chronic wounds also lead to the formation of necrotic tissue, which in turn lead to growth of microbes. Debridement of necrotic tissue is deemed as an important wound bed preparation for successful wound healing. Sharp and surgical debridement rapidly remove necrotic tissue and reduce the bacterial burden, but also carry the greatest risk of damage to viable tissue and require high levels of technical skill. Chemical, mechanical and autolytic debridement are frequently regarded as safer options, although the risk to the patient of ongoing wound complications is greater.

Additionally, the collagenase family of Metalloproteinases (MMP's) are a class of enzymes which are able to cleave native collagen into fragments. These fragments may then spontaneously denature into gelatin. Gelatin peptides are further cleaved by gelatinases such as MMP-2. Since the dry weight of skin is composed of 70–80% collagen, and since necrotic tissue is anchored to the wound bed by collagen fibers, enzymes which cleave collagen may be beneficial and assist in the debridement of this tissue. However, in chronic non-healing wounds, the levels and activity of collagenases are insufficient for the removal of necrotic tissue. Jung K, Knoll A G, *Considerations for the use of Clostridial collagenase in clinical practice*. Clin Drug Invest 1998; 15:245–252. Also, wound fluid from diabetics, for example, may have decreased MMP-2 activity. Furthermore, while exogenous application of collagenase has been proposed, its application suffers from the drawback of not being selective and risk the cleavage of collagen anchoring healthy cells in addition to necrotic tissue.

In the 1980's, it was discovered by researchers that the endothelium tissue of the human body produced nitric oxide (NO), and that NO is an endogenous vasodilator, namely, an agent that widens the internal diameter of blood vessels. NO is most commonly known as an environmental pollutant that is produced as a byproduct of combustion. At low concentrations such as less than 100 ppm, researchers have discovered that inhaled NO can be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD).

While NO has shown promise with respect to certain medical applications, delivery methods and devices must cope with certain problems inherent with gaseous NO delivery. First, exposure to high concentrations of NO may be toxic, especially exposure to NO in concentrations over 1000 ppm. Even lower levels of NO, however, can be harmful if the time of exposure is relatively high. For example, the Occupational Safety and Health Administration (OSHA) has set exposure limits for NO in the workplace at 25 ppm time-weighted averaged for eight (8) hours. It is extremely important that any device or system for delivering NO include features that prevent the leaking of NO into the surrounding environment. If the device is used within a closed space, such as a hospital room or at home, dangerously high levels of NO can build up in a short period of time. One concern over NO toxicity is the binding of NO, when absorbed into the circulation system such as through inhalation, to hemoglobin that give rise to methemoglobin Another problem with the delivery of NO is that NO rapidly oxidizes in the presence of oxygen to form $NO_2$, which is highly toxic, even at low levels. If the delivery device contains a leak, unacceptably high levels $NO_2$ of can develop. In addition, to the extent that NO oxidizes to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Accordingly, there is a need for a device and method for the treatment of surface and subsurface infections and wounds by the topical application of NO. The device is preferably leak proof to the largest extent possible to avoid a dangerous build up of NO and $NO_2$ concentrations. In addition, the device should deliver NO to the infected region of the patient without allowing the introduction of air that would otherwise react with NO to produce $NO_2$. The application of NO to the infected region preferably decreases the time required to heal the infected area by reducing pathogen levels. The device preferably includes a NO and $NO_2$ absorber or scrubber that will remove or chemically alter NO and $NO_2$ prior to discharge of the air from the delivery device.

SUMMARY OF THE INVENTION

It has been discovered that NO will interfere with or kill the growth of bacteria grown in vitro and has been investigated for its use as a sterilizing agent. PCT International Application No. PCT/CA99/01123 published Jun. 2, 2000, by one of the named inventors of the present application, discloses a method and apparatus for the treatment of respiratory infections by NO inhalation.

Topical exposure of nitric oxide gas to wounds such as chronic non-healing wounds may be beneficial in promoting healing of the wound and in preparing the wound bed for further treatment and recovery. Nitric oxide gas may be used, for example, to reduce the microbial infection and burden on these wounds, manage exudate secretion by reducing inflammation, upregulate expression of endogenous collagenase to locally debride the wound, and regulate the formation of collagen.

In a first aspect of the invention, a device for the topical delivery of nitric oxide gas to an infected area of skin includes a source of nitric oxide gas, a bathing unit, a flow control valve, and a vacuum unit. The bathing unit is in fluid communication with the source of nitric oxide gas and is adapted for surrounding the area of infected skin and forming a substantially air-tight seal with the skin surface. The flow control valve is positioned downstream of the source of nitric oxide and upstream of the bathing unit for controlling the amount of nitric oxide gas that is delivered to the bathing unit. The vacuum unit is positioned downstream of the bathing unit for withdrawing gas from the bathing unit.

In a second aspect of the invention, the device according to the first aspect of the invention includes a controller for controlling the operation of the flow control valve and the vacuum unit.

In a third aspect of the invention, the device according to the first aspect of the invention further includes a source of diluent gas and a gas blender. The diluent gas and the nitric oxide gas are mixed by the gas blender. The device also includes a nitric oxide gas absorber unit that is positioned upstream of the vacuum unit. The device also includes a controller for controlling the operation of the flow control valve and the vacuum unit.

In a fourth aspect of the invention, a method of delivering an effective amount of nitric oxide to an infected area of skin includes the steps of providing a bathing unit around the infected area of skin, the bathing unit forming a substantially air-tight seal with the skin. Gas containing nitric oxide is then transported to the bathing unit so as to bathe the infected area of skin with gaseous nitric oxide. Finally, at least a portion of the nitric oxide gas is evacuated from the bathing unit.

In a fifth aspect of the invention a method of treating infected tissue with topical nitric oxide exposure includes the steps of providing a source of nitric oxide containing gas and delivering the nitric oxide containing gas to a skin surface containing infected tissue so as to bathe the infected tissue with nitric oxide.

In a sixth aspect of the invention, a method of treating wounds with topical nitric oxide exposure includes the steps of providing a source of nitric oxide containing gas and delivering the nitric oxide containing gas to the wound so as to bathe the wound with nitric oxide. Preferably, the treatment method includes continuous exposure of the wound to a sufficiently high concentration of nitric oxide gas for a sufficient amount of time to kill or effect a 2–3 $\log_{10}$ reduction in the microorganism population at the wound site, without significant toxicity to the subject or the host cells of the treated subject. For example, the high concentration of nitric oxide gas may range from about 120 ppm to about 400 ppm, and more preferably at about 200 ppm to 250 ppm. The amount of time for the exposure of nitric oxide may also range from 5 hours to 96 hours, yet optimal exposure time and concentration can be determined based on the individual condition of the subject as prescribed by a physician. In another embodiment, the treatment method may also include a second treatment period, subsequent to the first treatment period with high concentration of nitric oxide gas, in which the wound is treated with a lower concentration of nitric oxide gas. Preferably, the lower concentration of nitric oxide gas ranges from 1 ppm to 80 ppm, and more preferably ranges from 5 ppm to 20 ppm. The exposure time for the second treatment period may also range from 5 hours to 96 hours, depending on the individual condition of the treated subject. In another embodiment, the wound is exposed to 200 ppm of nitric oxide gas for about 7–8 hours preferably during the night while the patient sleeps, and nitric oxide exposure may be withdrawn during the day time, or provided at a low concentration (e.g., 5 ppm to 20 ppm) for about 5–16 hours.

In a seventh aspect of the invention, a method of managing exudate secretion in a wound with topical exposure of nitric oxide includes the steps of removing excess exudate, dressing the wound with a gas permeable dressing, providing a source of nitric oxide containing gas, and delivering the nitric oxide containing gas to the wound so as to bathe the wound with nitric oxide.

In an eighth aspect of the invention, a method of debriding a wound with topical exposure of nitric oxide includes the steps of providing a source of nitric oxide containing gas, and delivering the nitric oxide containing gas to the wound so as to upregulate the expression of endogenous enzymes such as collagenase and gelatinase by the host cells located locally at the wound site of the treated subject. Preferably, the treatment method includes exposure of the wound to a sufficiently high concentration of nitric oxide gas for a sufficient amount of time to upregulate expression of endogenous collagenase without significant toxicity to the host cells of the treated subject. For example, the high concentration of nitric oxide gas may range from 120 ppm to 400 ppm, and more preferably at about 200 ppm–250 ppm. The amount of time for the exposure of nitric oxide may also range from 5 hours to 72 hours, yet optimal exposure time and concentration can be determined based on the individual condition of the subject as prescribed by a physician. Preferably, the expression of collagenase in the host cells may be monitored by taking biopsies and analyzing the expression of collagenase MRNA or protein through a various of techniques available in the art, such as Northern blot, RT-PCR, quantitative RT-PCR, immunostaining, immunoprecipitation, or ELISA. Additionally, after the treatment period with the high concentration of nitric oxide gas, the wound may also be exposed to a lower concentration for a second treatment period so as to reduce collagenase expression and increase collagen expression.

In a ninth aspect of the invention, a method for wound bed preparation with topical nitric oxide exposure includes the steps of providing a source of nitric oxide gas and delivering the nitric oxide containing gas to the wound.

In a tenth aspect of the invention, a method of reducing scarring in the healing process of a wound with topical nitric oxide exposure includes providing a source of nitric oxide gas, exposing the wound to a high concentration of exogenous nitric oxide gas for a treatment period without inducing toxicity to the subject or to healthy cells surrounding the wound, exposing the wound to a decreased concentration of exogenous nitric oxide gas for a second treatment period sufficient to increase the expression of collagen mRNA; and exposing the wound to a third concentration of exogenous nitric oxide gas for a third treatment period, wherein the third concentration is between the high concentration and the decreased concentration. The high concentration preferably ranges from about 200 ppm to 400 ppm, the decreased concentration preferably ranges from about 5–20 ppm, and the third concentration ranges from about 20 ppm to 200 ppm. Also, the first treatment period is preferably at least seven hours in a day, and the second and third treatment periods, each preferably ranges from about 5–12 hours in a day. The three step treatment may also be provided for multiple days, and preferably for at least 3–14 days.

It is an object of the invention to provide a delivery device for the topical delivery of a NO-containing gas to any exposed wounds on the skin surface or subsurface, or any exposed surface of the body such as the eye, or any exposed internal organs of the body. It is a further object of the device to prevent the NO-containing gas from leaking from the delivery device. The method of delivering an effective amount of nitric oxide gas to the infected or wounded area kills bacteria and other pathogens and promotes the healing process.

BRIEF DESCRIPTION OF THE DRAWINGS

FIG. 2 illustrates a bathing unit surrounding the foot of a patient.

FIG. 3 illustrates a bathing unit surrounding the hand of a patient.

FIG. 9 illustrates wound bacterial content following topical application of 200 ppm gNO in a full thickness infected wound model in rabbits.

FIG. 10 shows wound bacterial content following topical application of 400 ppm gNO in a full thickness infected wound model in rabbits.

FIG. 14 shows MRNA expression for collagen and collagenase following exposure to 200 ppm gNO for 24 hours and 48 hours.

FIG. 15 illustrates the morphology of fibroblast cells exposed inside gNO chamber to less than 200 ppm NO versus control group inside conventional tissue culture incubator.

DETAILED DESCRIPTION OF THE PREFERRED EMBODIMENTS

Figure 1:
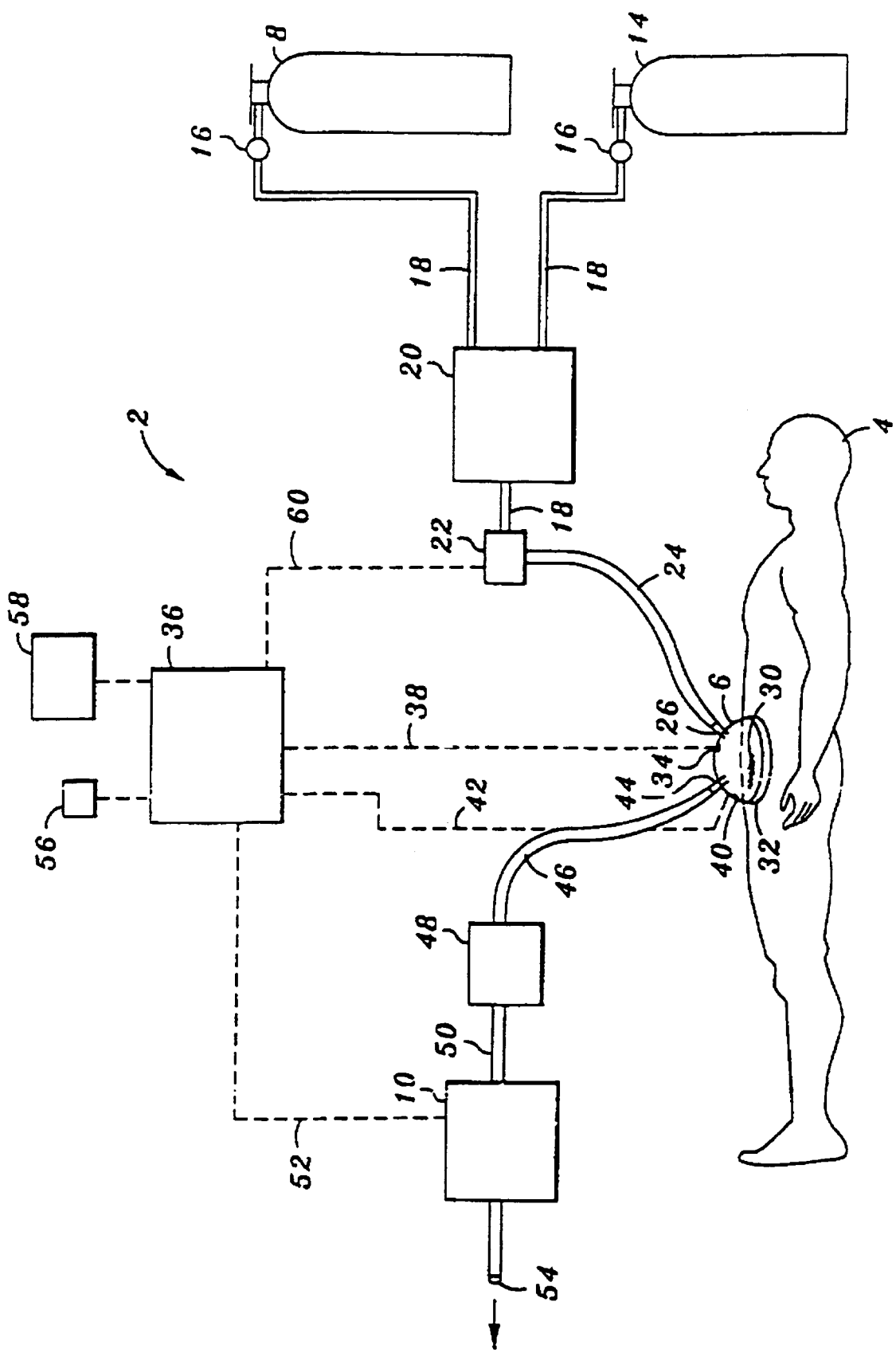
FIG. 1 illustrates a schematic representation of the NO delivery device according to one aspect of the invention.

Referring now to FIG. 1, a NO delivery device 2 is shown connected to a patient 4. In its most general sense, the NO delivery device 2 includes a bathing unit 6 that is fluidically connected to a NO gas source 8, a flow control valve 22, and a vacuum unit 10. FIG. 1 illustrates one preferred embodiment of the invention.

In FIG. 1, the NO gas source 8 is a pressurized cylinder containing NO gas. While the use of a pressurized cylinder is the preferred method of storing the NO-containing gas source 8, other storage and delivery means, such as a dedicated feed line (wall supply) can also be used. Typically, the NO gas source 8 is a mixture of $N_2$ and NO. While $N_2$ is typically used to dilute the concentration of NO within the pressurized cylinder, any inert gas can also be used. When the NO gas source 8 is stored in a pressurized cylinder, it is preferable that the concentration of NO in the pressurized cylinder fall within the range of about 800 ppm to about 2500 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen. Pressurized cylinders containing low concentrations of NO (e.g., less than 100 ppm NO) can also be used in accordance with the device and method disclosed herein. Of course, the lower the concentration of NO used, the more often the pressurized cylinders will need replacement.

FIG. 1 also shows source of diluent gas 14 as part of the NO delivery device 2 that is used to dilute the concentration of NO. The source of diluent gas 14 can contain $N_2$, $O_2$, Air, an inert gas, or a mixture of these gases. It is preferable to use a gas such as $N_2$ or an inert gas to dilute the NO concentration since these gases will not oxidize the NO into $NO_2$ as would $O_2$ or air. The source of diluent gas 14 is shown as being stored within a pressurized cylinder. While the use of a pressurized cylinder is shown in FIG. 1 as the means for storing the source of diluent gas 14, other storage and delivery means, such as a dedicated feed line (wall supply) can also be used.

The NO gas from the NO gas source 8 and the diluent gas from the diluent gas source 14 preferably pass through pressure regulators 16 to reduce the pressure of gas that is admitted to the NO delivery device 2. The respective gas streams pass via tubing 18 to an optional gas blender 20. The gas blender 20 mixes the NO gas and the diluent gas to produce a NO-containing gas that has a reduced concentration of NO. Preferably, the NO-containing gas that is output from the gas blender 20 has a concentration that is less than about 400 ppm and more preferably about 200 ppm. Depending on the concentration needed for the specific application, the concentration of NO-containing gas that is output from the gas blender 20 can also be regulated to less than about 100 ppm or less than about 40 ppm, if desired.

The NO-containing gas that is output from the gas blender 20 travels via tubing 18 to a flow control valve 22. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the NO-containing gas that is input to the bathing unit 6. The NO-containing gas leaves the flow control valve 22 via flexible tubing 24. The flexible tubing 24 attaches to an inlet 26 in the bathing unit 6. The inlet 26 might include an optional one way valve 64 (see FIG. 3) that prevents the backflow of gas into the tubing 24.

Still referring to FIG. 1, the bathing unit 6 is shown sealed against the skin surface of a patient 4. The infected area 30 which can be an abscess, lesion, wound, or the like, is enclosed by the bathing unit 6. The bathing unit 6 preferably includes a seal portion 32 that forms a substantially air-tight seal with the skin of the patient 4, or any other exposed surface of the body (e.g., eye) or exposed internal organs desired to be treated. Substantially air-tight is meant to indicate that the NO-containing gas does not leak out of the bathing unit 6 in significant amounts (i.e., no more than about 5% of the NO-containing gas delivered to the bathing unit 6). The seal portion 32 may comprise an inflatable seal 61, such as that shown in FIGS. 2 and 3, or alternatively the seal portion 32 may comprise a flexible skirt or the like that confirms to the surface of the patient 4. The seal portion 32 also might include an adhesive portion that adheres to the skin surface of a patient 4. In other envisioned embodiments, the sealing portion 32 may merely comprise the interface of the bathing unit 6 with the surface of the patient's 4 skin.

The bathing unit 6 can be made of a virtually limitless number of shapes and materials depending on its intended use. The bathing unit 6 might be formed as a rigid structure, such as that shown in FIG. 1, that is placed over the infected area 30. Alternatively, the bathing unit 6 can be formed of a flexible, bag-like material that is inflatable over the infected area 30. FIG. 2 shows such a structure in the shape of a boot that is placed over the patient's 4 foot. FIG. 3 shows another inflatable bathing unit 6 that is formed in the shape of a mitten or glove that is worn over the patient's 4 hand.

In one preferred embodiment of the invention, the bathing unit 6 includes an NO sensor 34 that measures the concentration of NO gas within the bathing unit 6. The NO sensor 34 preferably reports this information to a controller 36 via signal line 38. An optional $NO_2$ sensor 40 can also be included within the bathing unit 6. The $NO_2$ sensor 40 preferably reports the concentration of $NO_2$ to the controller 36 via signal line 42. The sensors 40, 42 can be a chemiluminesense-type, electrochemical cell-type, or spectrophotometric-type sensor.

The bathing unit 6 also includes an outlet 44 that is used to remove gas from the bathing unit 6. The outlet 44 is preferably located away from the gas inlet 26 such that NO gas does not quickly enter and exit the bathing unit 6. Preferably, the inlet 26 and outlet 44 are located in areas of the bathing unit 6 such that the NO gas has a relatively long residence time. Flexible tubing 46 is connected to the outlet 44 and provides a conduit for the removal of gases from the bathing unit 6.

In one preferred embodiment of the invention, the flexible tubing 46 is in fluid communication with an absorber unit 48. The absorber unit 48 preferably absorbs or strips NO from the gas stream that is exhausted from the bathing unit 6. It is also preferable for the absorber unit 48 to also absorb or strip $NO_2$ from the gas stream that is exhausted from the bathing unit 6. Since these gases are toxic at high levels, it is preferable that these components are removed from the delivery device 2 prior to the gas being vented to the atmosphere. In addition, these gases can react with the internal components of the vacuum unit 10 and interfere with the operation of the delivery device 2.

The now clean gas travels from the absorbing unit 48 to the vacuum unit 10 via tubing 50. The vacuum unit 10 provides a negative pressure within the tubing 50 so as to extract gases from the bathing unit 6. The vacuum unit 10 is preferably controllable with respect to the level of vacuum or suction supplied to the tubing 50 and bathing unit 6. In this regard, in conjunction with the flow control valve 22, the amount of NO gas within the bathing unit 6 can be regulated. Preferably, the vacuum unit 10 is coupled with the controller 36 via a signal line 52. The controller 36, as discussed below, preferably controls the level of output of the vacuum unit 10. The gas then passes from the vacuum unit 10 to a vent 54 that is open to the atmosphere.

It should be understood that the absorbing unit 48 is an optional component of the delivery device 2. The gas laden with NO and $NO_2$ does not have to be removed from the gas stream if there is no concern with local levels of NO and $NO_2$. For example, the gas can be exhausted to the outside environment where high concentrations of NO and $NO_2$ will not develop. Alternatively, a recirculation system (not shown) might be used to recycle NO with the bathing unit 6.

Still referring to FIG. 1, the delivery device 2 preferably includes a controller 36 that is capable of controlling the flow control valve 22 and the vacuum unit 10. The controller 36 is preferably a microprocessor-based controller 36 that is connected to an input device 56. The input device 56 is used by an operator to adjust various parameters of the delivery device such as NO concentration, residence or exposure time of NO, pressure within the bathing unit 6, etc. An optional display 58 can also be connected with the controller 36 to display measured parameters and settings such as the set-point NO concentration, the concentration of NO within the bathing unit 6, the concentration of $NO_2$ within the bathing unit 6, the flow rate of gas into the bathing unit 6, the flow rate of gas out of the bathing unit 6, the total time of delivery, and the like.

The controller 36 preferably receives signals from sensors 34, 40 regarding gas concentrations if such sensors 34, 40 are present within the delivery device 2. Signal lines 60, 52 are connected to the flow control valve 22 and vacuum unit 10 respectively for the delivery and receipt of control signals.

In another embodiment of the invention, the controller 36 is eliminated entirely. In this regard, the flow rate of the gas into the bathing unit 6 and the flow rate of the gas out of the bathing unit 6 are pre-set or adjusted manually. For example, an operator can set a vacuum output that is substantially equal to the flow rate of the gas delivered to the bathing unit 6 via the flow control valve 22. In this manner, NO gas will be able to bathe the infected area 30 without any build-up or leaking of NO or $NO_2$ gas from the delivery device 2.

Figure 4:
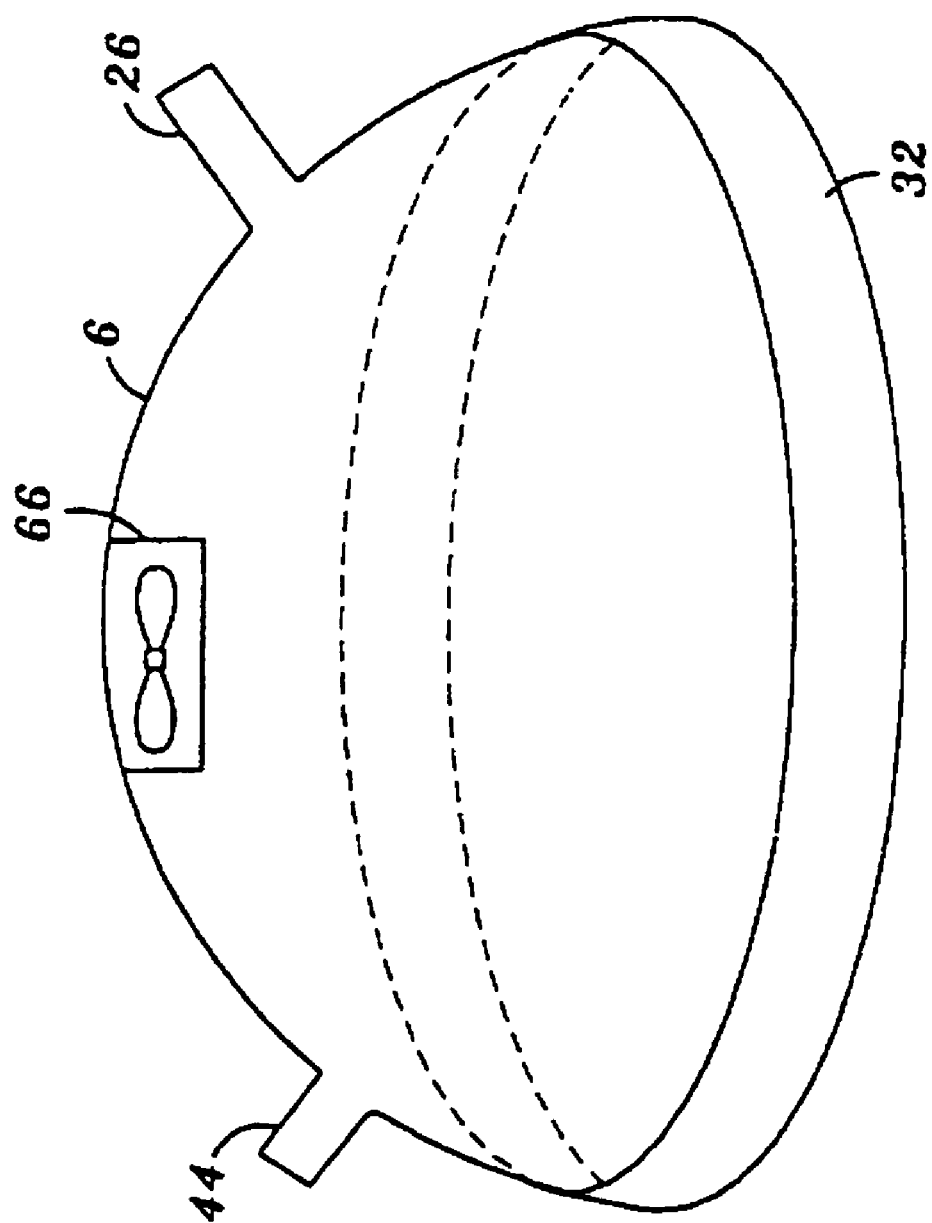
FIG. 4 illustrates a bathing unit including an agitator located therein.

FIG. 2 illustrates a bathing unit 6 in the shape of a boot that is used to treat an infected area 30 located on the leg of the patient 4. The bathing unit 6 includes an inflatable seal 61 that surrounds the leg region to make a substantially air-tight seal with the skin of the patient 4. This embodiment shows a nozzle 62 that is affixed near the inlet 26 of the bathing unit 6. The nozzle 62 directs a jet of NO gas onto the infected area 30. The jet of gaseous NO aids in penetrating the infected area 30 with NO to kill or inhibit the growth of pathogens. FIG. 3 shows another embodiment of the bathing unit 6 in the shape of a mitten or glove. The bathing unit 6 is also inflatable and contains an inflatable seal 61 that forms a substantially air-tight seal around the skin of the patient 4. FIG. 3 also shows an optional one way valve 64 located in the inlet 26. As seen in FIGS. 3 and 4, the inlet 26 and outlet 44 are located away from one another, and preferably on opposing sides of the treated area such that freshly delivered NO gas is not prematurely withdrawn from the bathing unit 6.

For treatment of an infected area 30, the bathing unit 6 is placed over the infected area 30. An air-tight seal is then formed between the skin of the patient 4 and the bathing unit 6. If the bathing unit 6 has an inflatable construction, the bathing unit 6 must be inflated with gas. Preferably, the bathing unit 6 is initially inflated only with the diluent gas to prevent the leaking of NO and $NO_2$ from the device 2. Once an adequate air-tight seal has been established, the operator of the device initiates the flow of NO from the NO gas source 8 to the bathing unit 6. As described above, this may be accomplished manually or via the controller 36.

Once the bathing unit 6 has started to fill with NO gas, the vacuum unit 10 is turned on and adjusted to the appropriate output level. For an inflatable bathing unit 6, the output level (i.e., flow rate) of the vacuum unit 10 should be less than or equal to the flow rate of NO gas entering the bathing unit 6 to avoid deflating the bathing unit 6. In embodiments of the device where the bathing unit 6 is rigid, the vacuum unit 10 can be set to create a partial vacuum within the bathing unit 4. In this regard, the partial vacuum helps to form the air-tight seal between the skin of the patient 4 and the bathing unit 6. Of course, the vacuum unit 10 can also be set to withdraw gas at a substantially equal rate as the gas is delivered to the bathing unit 6. An effective amount of NO is delivered to the bathing unit 6 to kill pathogens and/or reduce the growth rate of the pathogens in the infected area 30. Pathogens include bacteria, viruses, and fungi.

FIG. 4 shows another embodiment of the invention in which the bathing unit 6 includes an agitator 66 that is used to create turbulent conditions inside the bathing unit 6. The agitator 66 preferably is a fan-type of mechanism but can include other means of creating turbulent conditions within the bathing unit 6. The agitator 66 aids in refreshing the infected area 30 with a fresh supply of NO gas.

Examples of Nitric Oxide Applications

In chronic non-healing wound such as in patients suffering from diabetic lesions, a variety of factors can potentially influence wound healing, including infections, excessive exudate, necrotic tissue, poor tissue handling, and impaired tissue perfusion. Nitric oxide gas can be used to reduced the infection or microbial burden on the wound. While the examples discussed below are applications of nitric oxide to the skin, nitric oxide can also be topically applied to other surfaces of the body such as the eye, or any other exposed surface such as muscle, ligaments, tendons, and internal organs of the body that may be exposed, for example, due to cut, tear, or wound.

Figure 5:
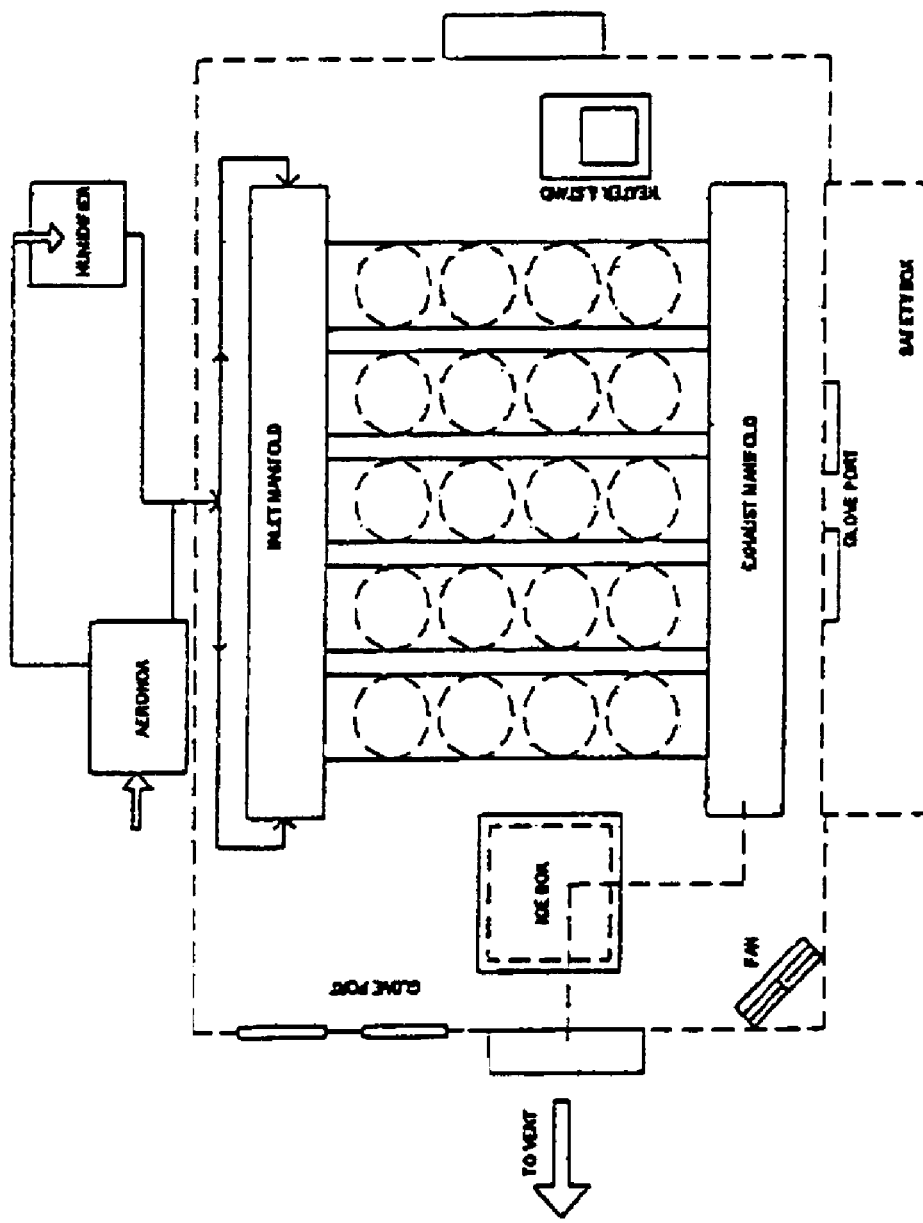
FIG. 5 shows a specialized gaseous nitric oxide (gNO) incubation chamber designed to conduct in vitro studies on the effects of gNO exposure on mammalian cell cultures as well as microbial cells under optimal growth conditions.

To study the effects of gaseous nitric oxide on potential pathogens, a custom gas exposure incubator was designed and validated for temperature, humidity, and gas concentrations, providing an environment that matches that of a microbiologic incubator, while enabling controlled exposure of precise concentrations of the gas. FIG. 5 shows a specialized gaseous nitric oxide (gNO) incubation chamber designed to conduct in vitro studies on the effects of gNO exposure on mammalian cell cultures as well as microbial cells under optimal growth conditions. The gNO chamber allowed control and adjustment of following factors in all in vitro studies: gNO dose, total air flow, $NO_2$ levels, $O_2$ levels, $CO_2$ levels, temperature, and humidity.

For the initial pilot studies, two strains of bacterial pathogen were selected based on two proposed clinical applications of gNO for respiratory infections and topical application. *P. aeruginosa* is associated primarily with pulmonary disease, but may also be associated with skin infection such as in severe burns. *S. aureus* is associated with surface wound infections. Both of these mcro-organisms were chosen for the pilot study.

The first step in the process of evaluating the direct effect of gNO on bacteria was to design a simple study to determine what dose, if any, would be an approximate lethal concentration level for microbes. Once an optimal dose was estimated, then a timing study would be conducted. For these initial studies, highly dense inoculums of *P. aeruginosa* and *S. aureus* suspensions ($10^8$ cfu/ml) were plated onto agar plates. These plates were then exposed to various concentrations of gNO in the exposure device in order to evaluate the effect on colony growth.

Figure 6:
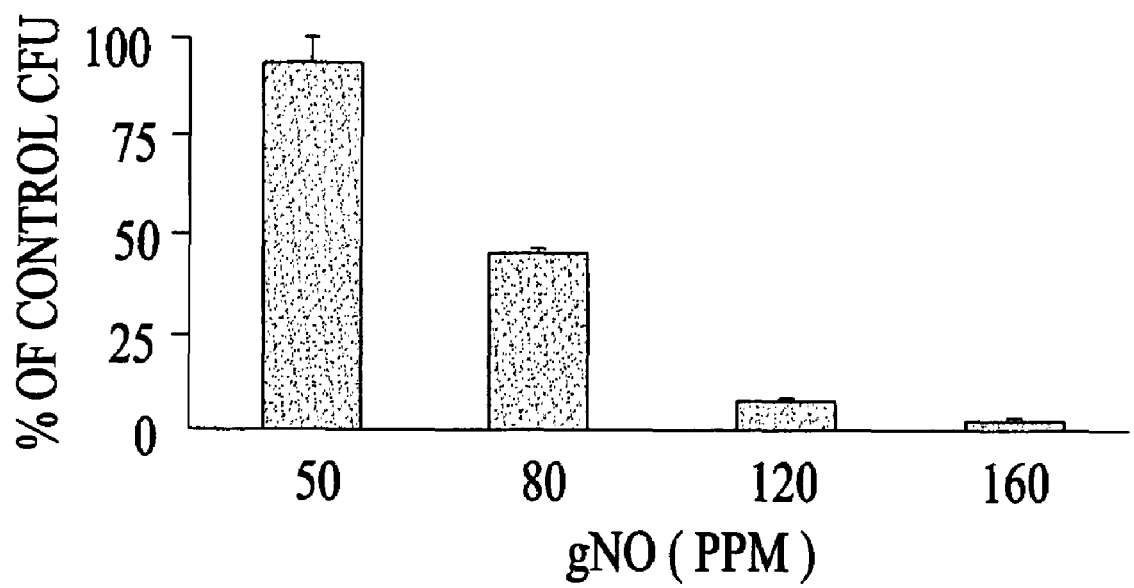
FIG. 6 depicts a S. aureus dosage curve for exposure to gaseous NO (gNO) with bacteria grown on solid media. Relative percentages of growth of S. aureus colony forming units (cfu) at 50, 80, 120 and 160 parts per million (ppm) of nitric oxide compared with growth of S. aureus cfu in medical air (100%) are shown.
Figure 7:
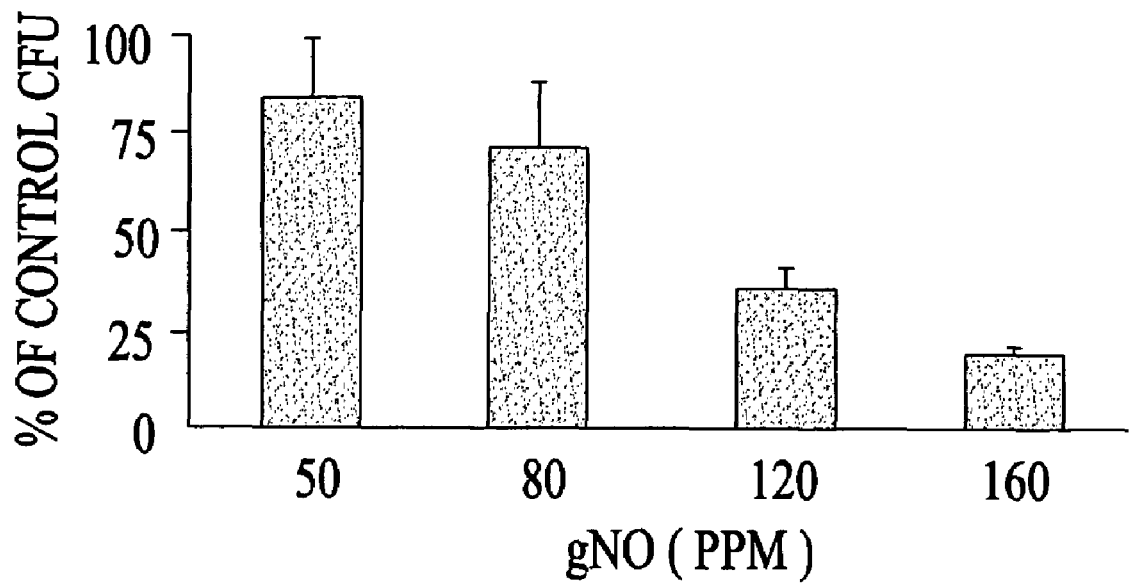
FIG. 7 depicts a *Pseudomonas aeruginosa* dosage curve for exposure to NO gas with bacteria grown on solid media. Relative percentages of growth of *P. aeruginosa* colony forming units (cfu) at 50, 80, 120 and 160 parts per million (ppm) of nitric oxide compared with growth of *P. aeruginosa* cfu in medical air (100%) are shown.
Figure 8A:
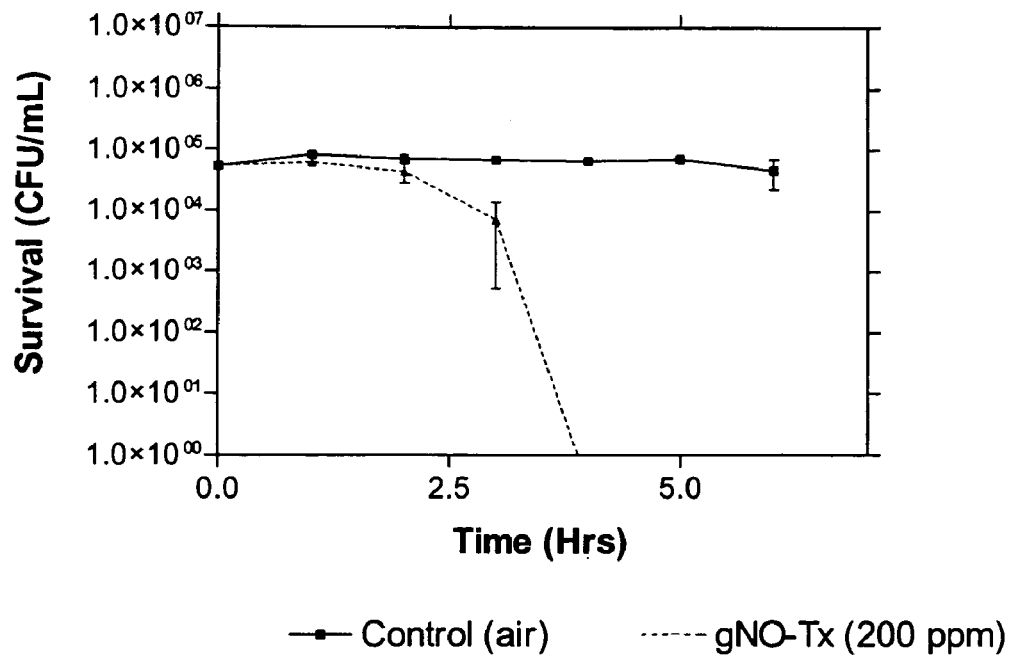
FIG. 8a–8m depict the bacteriocidal effect of 200 ppm gNO on a variety of microbes.
Figure 8B:
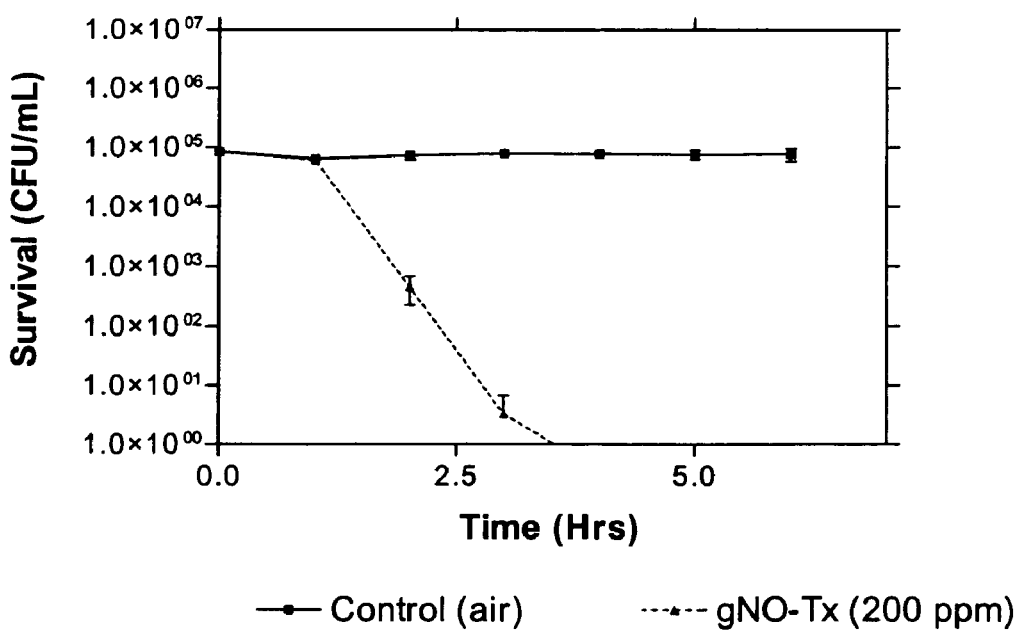
Figure 8C:
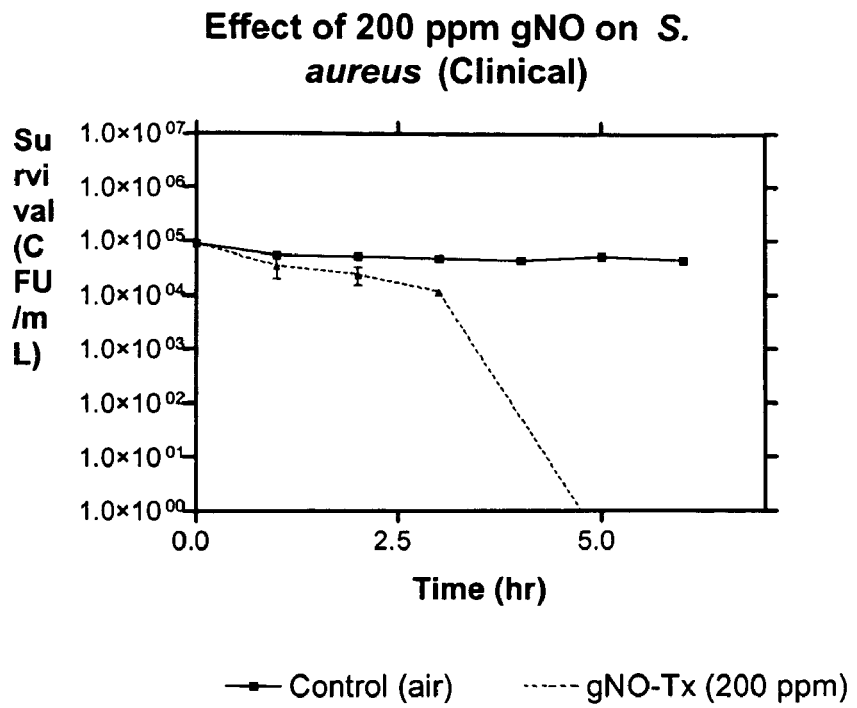
Figure 8D:
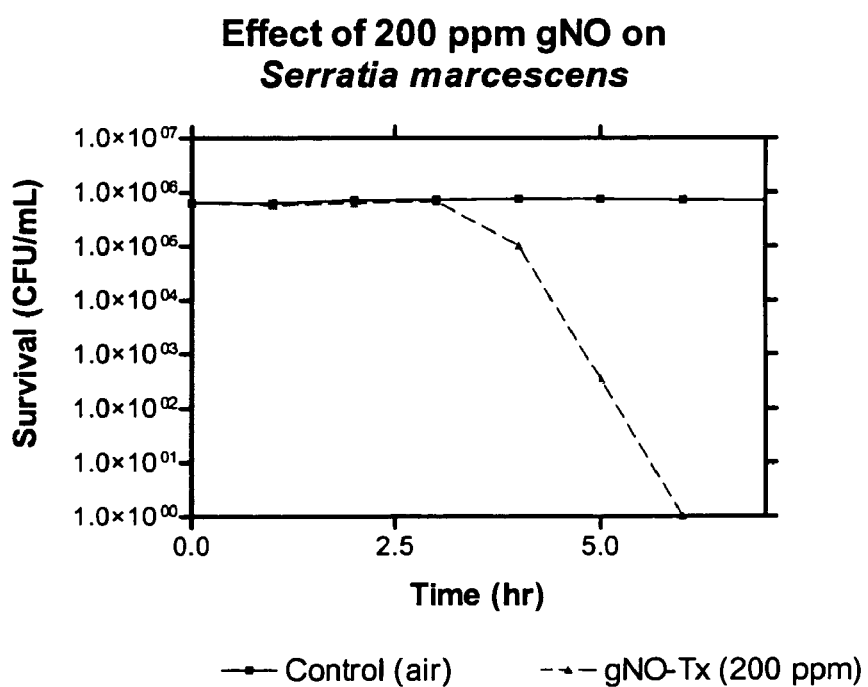
Figure 8E:
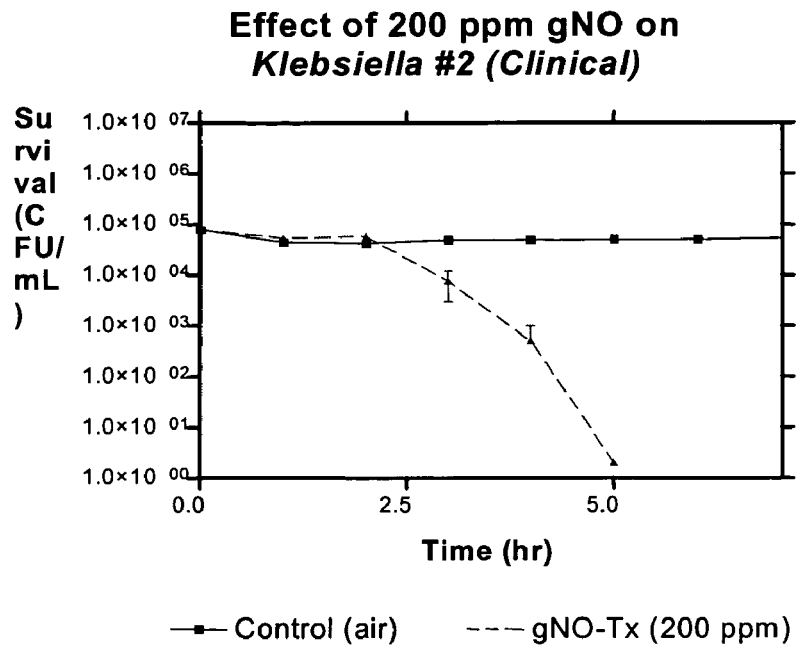
Figure 8F:
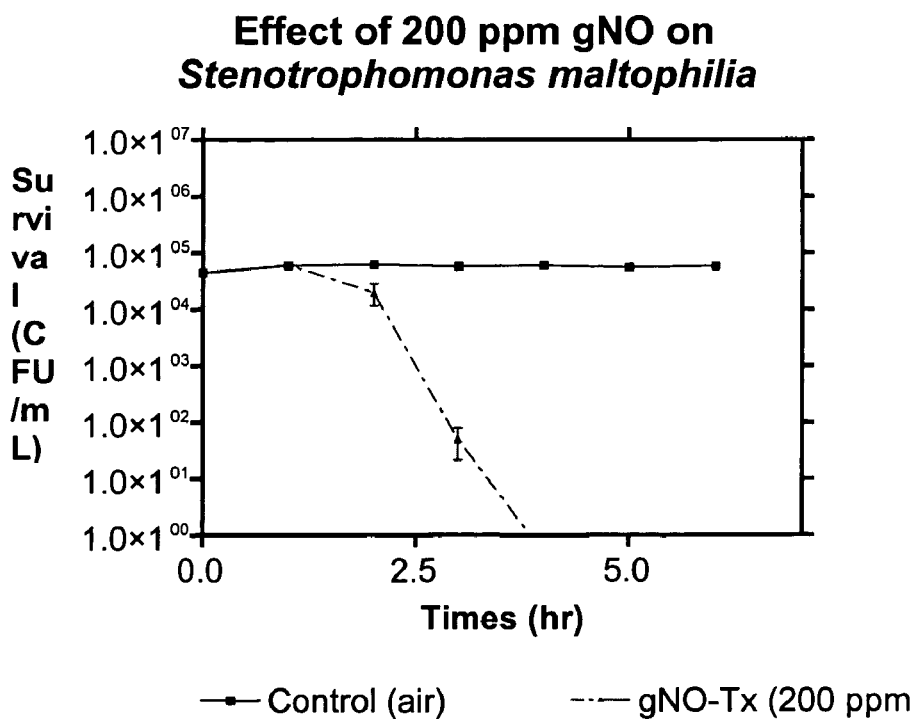
Figure 8G:
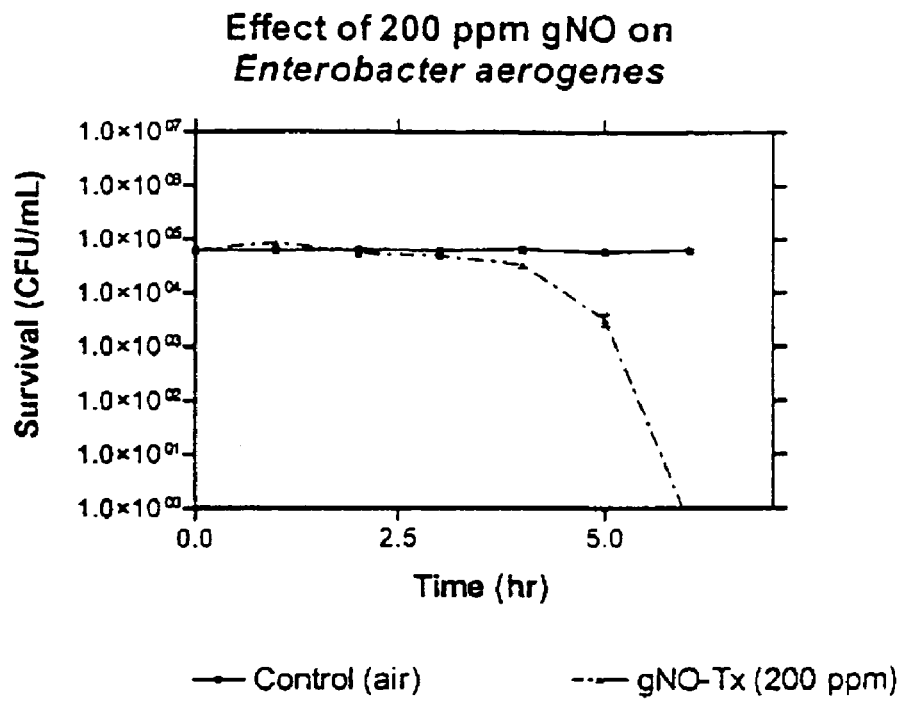
Figure 8H:
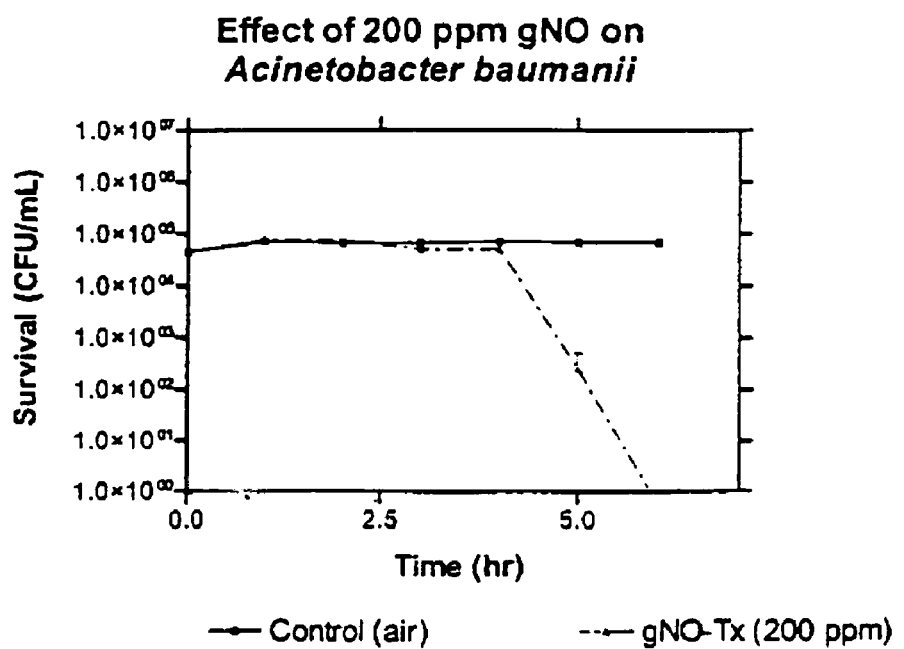
Figure 8I:
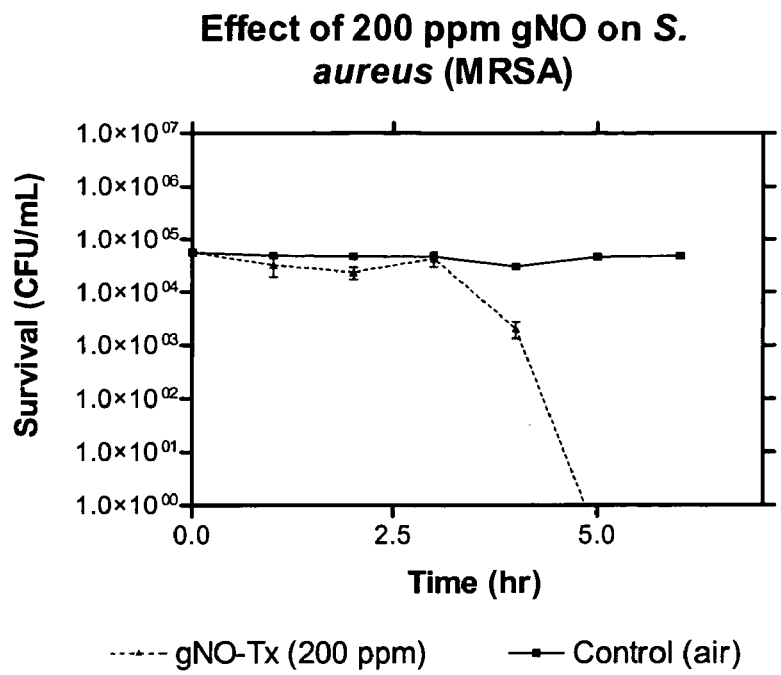
Figure 8J:
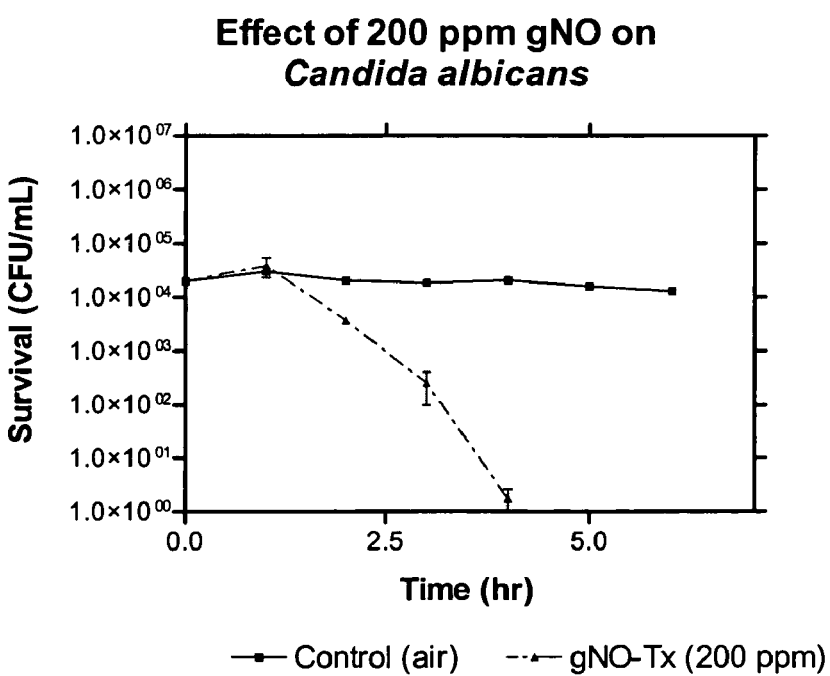
Figure 8K:
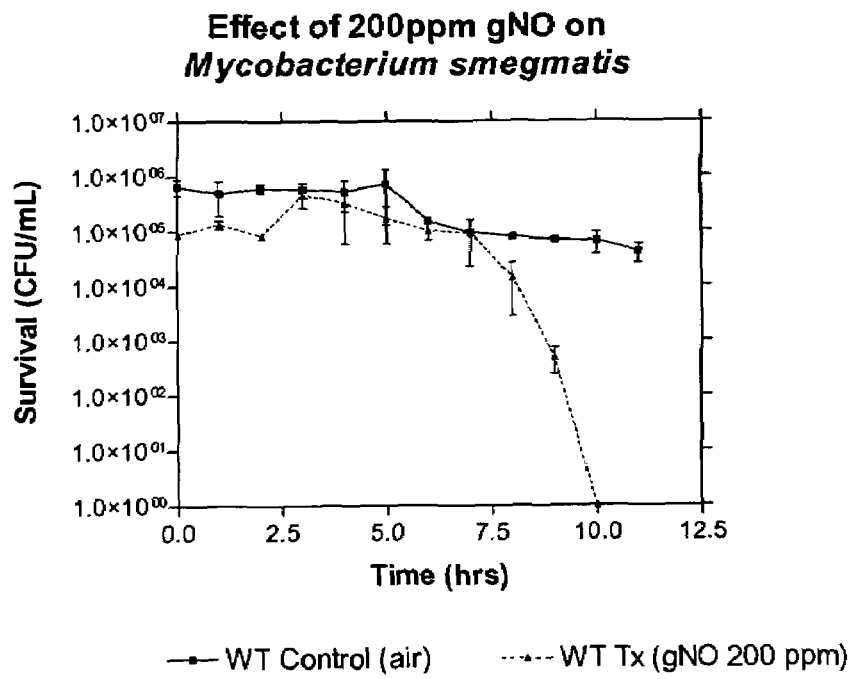
Figure 8L:
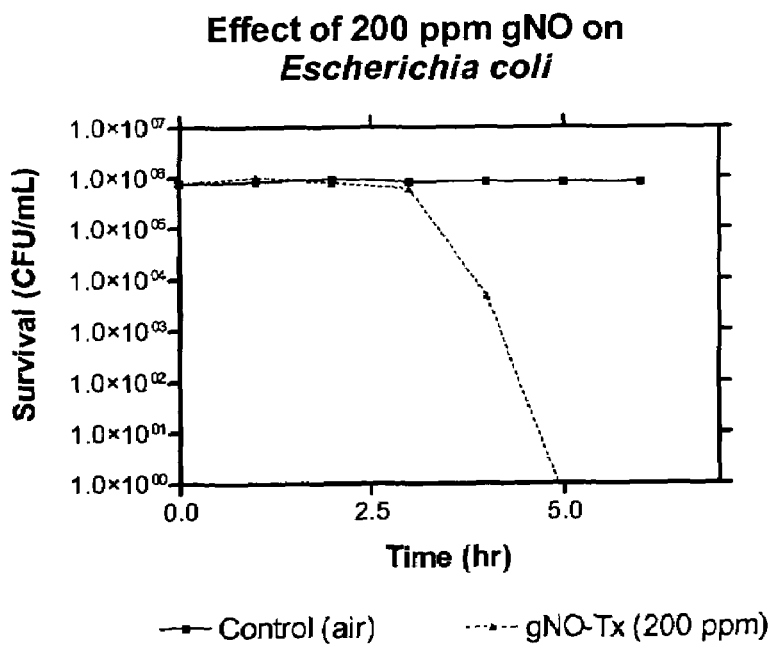
Figure 8M:
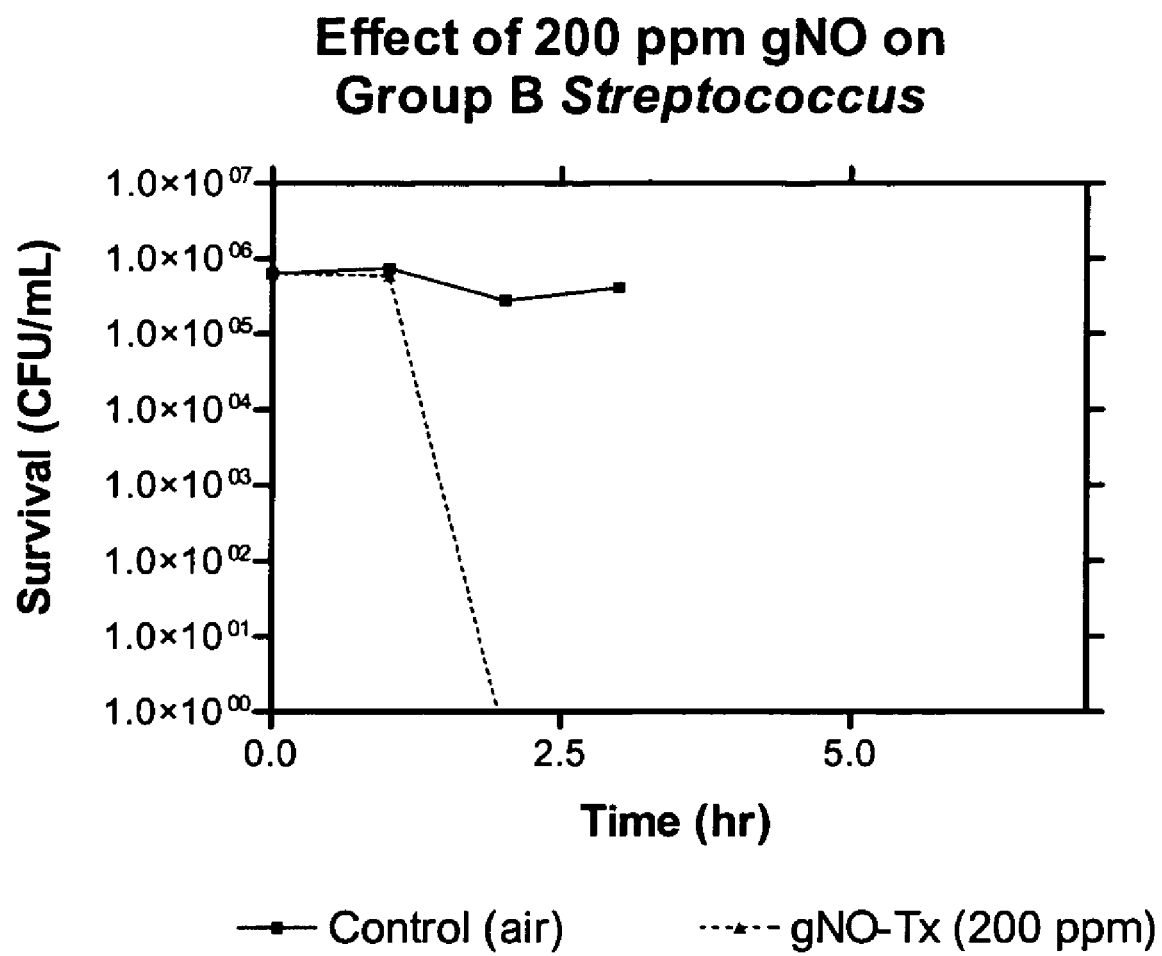

FIGS. 6 and 7 demonstrate that levels of gNO greater than 120 ppm reduced the colony formation of the bacteria by greater than 90%. Further studies indicated that the time required to achieve this affect occurred between 8–12 hours. These results confirm that gNO has an inhibitory effect on *P. aeruginosa* and *S. aureus* growth. Additionally, the data provide preliminary evidence that there is a time and dose relationship trend, with the amount of bacteriocidal activity increasing with increased time of exposure and concentration of gNO. That is, as the concentration of gNO increases, the number of colonies growing on the plates decreases.

Although there was a downward bacteriocidal trend towards 5–10% survival with increasing gNO to 120 ppm, none of the initial data showed a 100% bacteriocidal effect. Some bacteria may have survived because the materials and chemicals in the agar may have reacted with the gNO and buffered the effect. Of significance, was the observation that bacterial colonies remained the same in size and number after being transferred to a conventional incubator for 24 hours whereas controls increased in number and size to the degree that they could not be counted. This strongly suggested that gNO exposure prevented the growth of the bacteria, and may have killed the bacteria at some point during the gNO exposure. Accordingly, subsequent studies were designed to further study the bacteriocidal effects of gNO.

Following the dose and time ranging studies, a series of experiments were performed to determine the time required to effectively induce a bacteriocidal effect with 200 parts per million of gNO, a concentration just above the dose used in the dose-ranging study, on a representative collection of drug resistant gram-positive and gram-negative strains of bacteria associated with clinical infection. A successful bacteriocidal effect was defined as a decrease in bacteria greater than 3 $log_{10}$ cfu/ml. Further, *C. albicans*, Methicillin Resistant *S. aureus* (MRSA), a particularly resistant strain of *P. aeruginosa* from a cystic fibrosis patient, Group B *Streptococcus*, and *M. smegmatis* were also included to see if yeast, multi-drug resistant strains of bacteria, and actinomycetes have a similar response. The drug-resistant bacteria represent a variety of pathogens that contribute to both respiratory and wound infections.

For these experiments, saline was selected as a suspension media because it would not mask the direct effect of gNO as a bacteriocidal, whereas fully supplemented growth medium might introduce external variables (e.g., buffer or react with gNO). Other media might also provide metabolites and replenish nutrients that produce enzymes that protect bacteria from oxidative and nitrosative damage, thereby masking the effect of gNO. Furthermore, it has been suggested that a saline environment more realistically represents the hostile host environment to which bacteria are typically exposed in vivo. In saline, the colonies were static but remained viable. This is similar to the approach of Webert and Jean's use of animal models. Webert K E, et al (2000), *Effects of inhaled nitric oxide in a rat model of Pseudomonas aeruginosa pneumonia*, Crit Care Med, 28(7):2397–2405 and Jean D, et al., (2002) *Beneficial effects of nitric oxide inhalation on pulmonary bacterial clearance*, Critical Care Medicine. 30(2):442–7.

FIG. 8 shows the results of these experiments with the line plotted by square-shaped points representing survival curves of the control exposure microorganisms and the line plotted in triangle-shaped points representing the survival curves of the NO exposed microorganisms. These studies showed that gNO at 200 ppm had a completely bacteriocidal effect on all microorganisms tested. Without exception, every bacteria challenged with 200 ppm gNO had at least a three $\log_{10}$ reduction in cfu/ml and every test resulted in a complete and total cell death of all bacteria. These results were also characterized by a period of latency when it appeared that the bacteria were unaffected by gNO exposure (Table 1). The latent period was then followed by an abrupt death of all cells. Gram negative and gram positive bacteria, antibiotic resistant bacterial strains, yeast and mycobacteria were all susceptible to 200 ppm gNO. Of importance, is the observation that the two drug resistant bacteria strains were also susceptible. Accordingly, these results show that gNO directly exhibits a non-specific lethal effect on a variety of potentially pathogenic microorganisms.

The study also indicates a significant difference in the lag period for mycobacteria compared to all other organisms. The lag period suggests that mycobacteria may have a mechanism that protects the cell from the cytotoxicity of gNO for a longer period than other bacteria. Applicants believe that there is a dose-time dependent gNO threshold reached within the cell at which point rapid cell death occurs. It is possible that this threshold occurs when the normal NO detoxification pathways of the bacteria are overwhelmed. These studies indicate and confirm that supraphysiologic levels of NO (provided exogenously, for example, via delivery of 120 ppm to 400 ppm exogenous NO) may be bacteriocidal on representative strains of drug resistant bacteria and the effect appears to be abrupt, lethal and non-specific on these bacteria.

TABLE 1

| Bacteria | Gram staining | Latent Period* (hrs) | -2.5 $\log_{10}$ (hrs) | $LD_{100}$ (Hrs) |
|---|---|---|---|---|
| S. aureus (ATCC) | Positive | 3 | 3.3 | 4 |
| P. aeruginosa (ATCC) | Negative | 1 | 2.1 | 3 |
| MRSA | Positive | 3 | 4.2 | 5 |
| Serracia sp. | Negative | 4 | 4.9 | 6 |
| S. aureus (Clinical) | Positive | 3 | 3.7 | 4 |
| Klebsiella sp. #1 | Negative | 3 | 3.5 | 6 |
| Klebsiella sp. #2 | Negative | 2 | 4.1 | 5 |
| Klebsiella sp. #3 | Negative | 3 | 5.1 | 6 |
| S. maltophilia | Negative | 2 | 2.8 | 4 |
| Enterobacter sp. | Negative | 4 | 5.3 | 6 |
| Acinetobacter sp. | Negative | 4 | 5 | 6 |
| E. coli | Negative | 3 | 4.2 | 5 |
| Group B Streptococci | Positive | 1 | 1.5 | 2 |
| Average | N/A | 2.77 | 3.82 | 4.77 |
| SD | N/A | 1.01 | 1.17 | 1.30 |
| Mycobacterium | Positive | 7 | 9.2 | 10 |

To achieve a lethal effect over a broad range of microbes, 200 ppm of nitric oxide gas is preferably exposed to the wound site for at least 7 hours continuously such as when the patient is asleep at night. Shorter times may be used with higher concentration such as 400 ppm. Longer treatment options may also be provided that span days. Depending on the subject, periods of breaks in between treatment may also be arranged.

In vivo studies in animal models have further shown the beneficial effects of nitric oxide gas. In an animal model, full-thickness cutaneous wounds (Set A: four rabbits with eight 8.0 mm punch biopsies & Set B: 4 rabbits with two 50×15 mm wounds) were made on each side of dorsal midline and infected with equal volume of Staphylococcus aureus suspension on day zero. On day one, treated groups in A and B were respectively exposed to 200 and 400 ppm gNO for total of three days. Set A was exposed for two 4-hour sessions, interrupted by 1-hour of rest, inside a specialized restraining exposure chamber. A 24-hour continuous delivery model was used for animals in Set B by design of a specialized wound patch. Control groups were only exposed to medical grade air with corresponding flow rate. Four random sample punch biopsies (8.0 mm) were collected on post wounding days 3 and analyzed for bacterial content. Another four punch biopsies from both wound and normal skin tissue were collected for fibroblast viability analysis and toxic effects of gNO.

FIG. 9 reveals data from the animal study on bacterial content of the wounds exposed to 200 ppm gNO continuously for 72 hours when compared to control group only exposed to medical air. A significant bacterial reduction is observed in treated wounds. Rabbits appeared comfortable and at ease during the therapy and no toxic effect or damage were observed in the skin of treated animals when compared to the control. $NO_2$ did not exceed safety limits, at any point of the study, set by Occupational Safety and Health Administration (<4.3±0.3 ppm). FIG. 10 shows similar set of data as seen in FIG. 9, but where animal wounds were exposed to 400 ppm of gNO therapy. On average well over 10 fold drop ($p<0.05$) in bacterial content is observed in comparison between control and treated groups.

Figure 11:
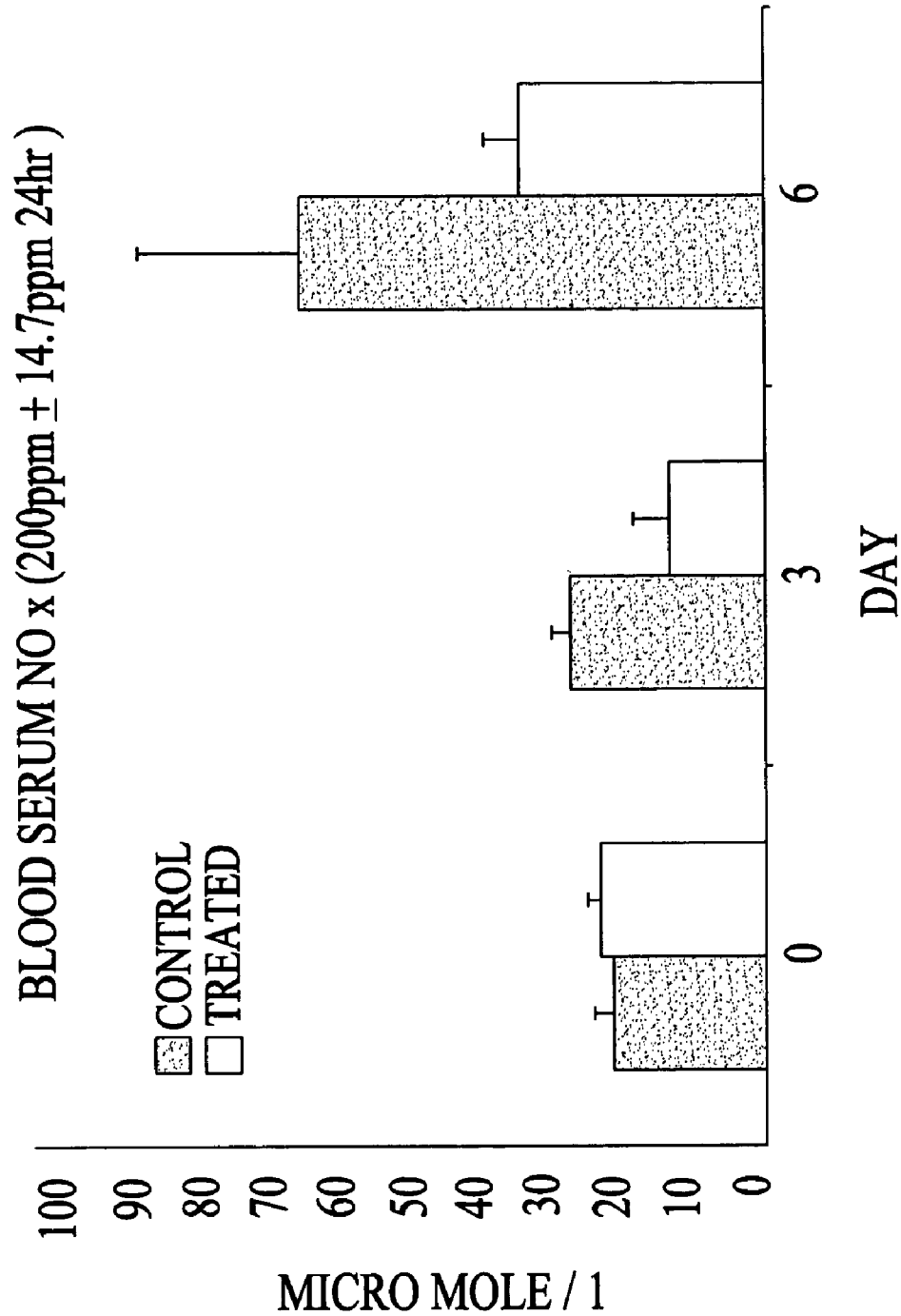
FIG. 11 shows rabbit blood serum NOx ($NO_2$ & $NO_3$) levels following topical application of 400 ppm gNO.

FIG. 11 demonstrates that nitrogen oxides levels ($NO_2$ and $NO_3$), one of end products of nitric oxide metabolism, measured in blood serum collected from the animals following exposure to 200 ppm gNO intermittently for 6 days. None of the samples show an increased level of NOx due to exposure to gNO indicating the fact that exposing full thickness wounds (8 at 8.0 mm in diameter) will not increase the nitric oxide level in animal's circulation system.

Figure 12:
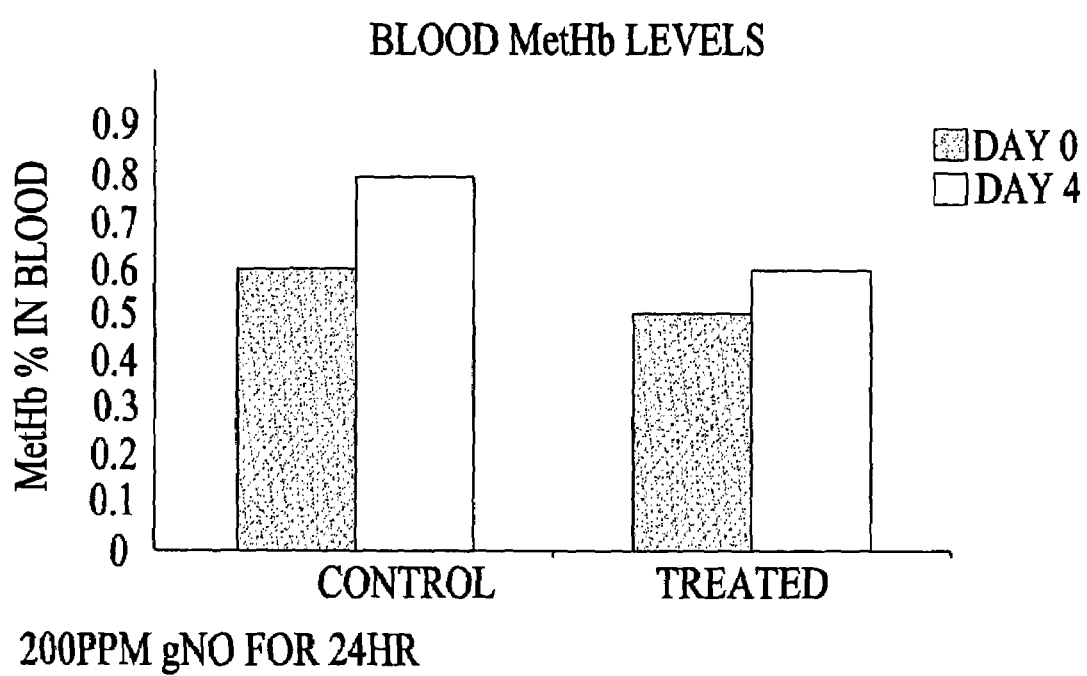
FIG. 12 illustrates rabbit blood methemoglobin levels following topical application of 400 ppm gNO on a full thickness infected wound model.

FIG. 12 indicates the level of methemoglobin (MetHb) in animal's blood following 6 day intermittent exposure to 200 ppm gNO. Animals in the treated group did not show an increase level of MetHB in comparison with the control group exposed to air. This further supports the data presented in FIG. 11 to the fact that topical application of gNO on open wounds did not contribute to an increase level of nitric oxide in the circulation and that the topical application of an open wound to about 200 ppm poses no significant toxicity concerns over the formation of methemoglobin.

Figure 13:
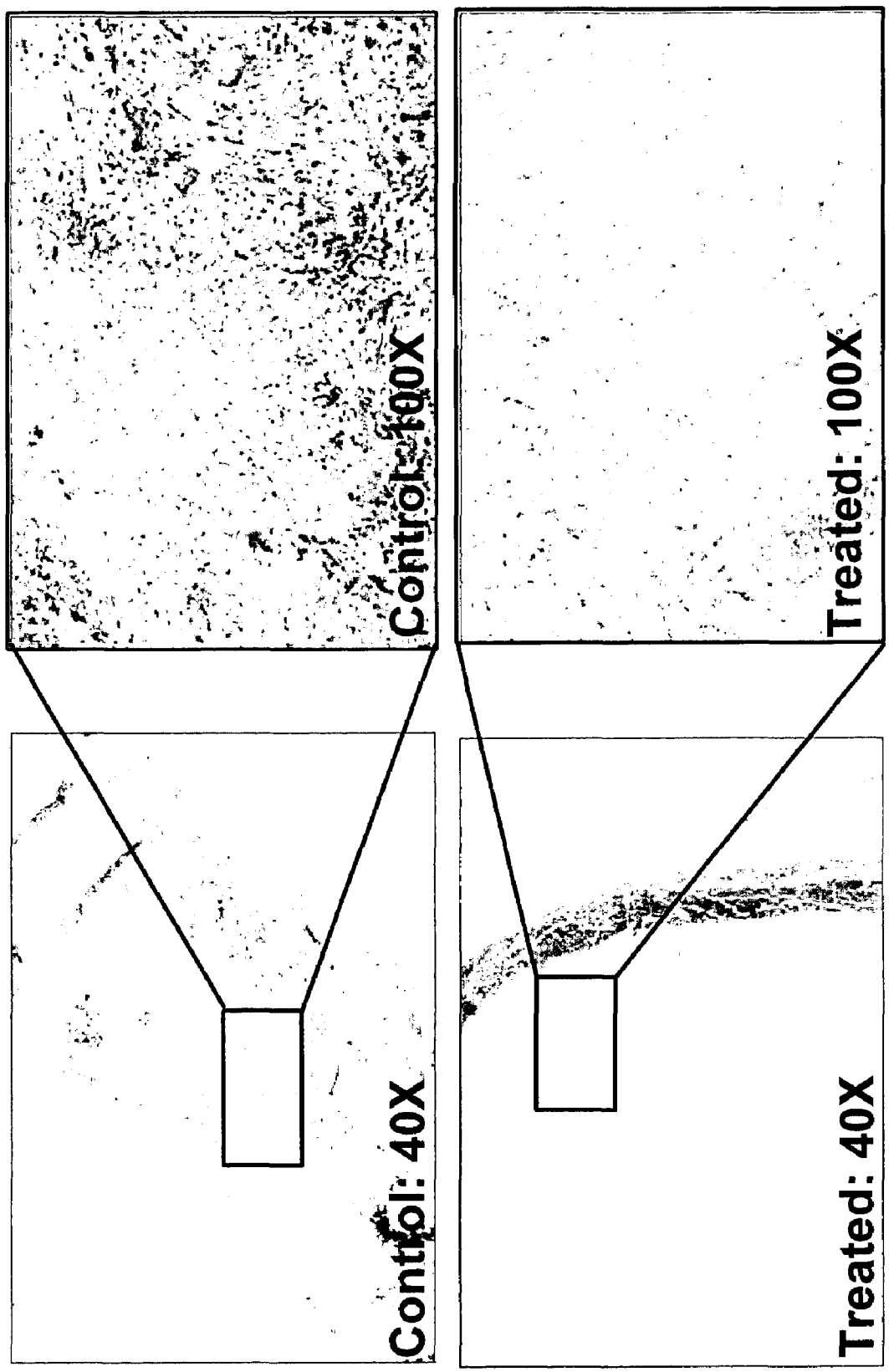
FIG. 13 illustrates histology analysis of full thickness infected wound exposed to 200 ppm gNO for 24 hours.

FIG. 13 presents histological analysis of tissue blocks prepared on wound punch biopsies from animals in treated and control groups. Samples from the control group show more advanced neutrophil infiltration and so a higher degree of inflammatory reaction. A lower level of neutrophil concentration is seen in wounds treated with gNO. Wounds treated with gNO also show a layer of scab closing on the wound, but control wounds remain open for longer period of time. Overall, a healthier healing process is observed in the wounds treated with gNO. No toxic effects (cellular debris due to apoptosis) can be seen in gNO treated group.

While the inflammatory response is integral to wound healing, an aberrant inflammatory response is believed to be one causal factor in chronic wounds and excess exudate. NO inhibits platelet aggregation, assists in maintaining vascular tone, and inhibits mast cell degranulation. Delledonne M, et al., (2003) *The functions of nitric oxide-mediated signaling and changes in gene expression during the hypersensitive response*, Antioxid Redox Signal, 5:33–41. and Hickey M J., (2001), *Role of inducible nitric oxide synthase in the regu-*

*lation of leukocyte recruitment*, Clin Sci (Lond), 100:1–12 NO produced constitutively by endothelial cells has been shown to have an on-going anti-inflammatory effect. Id. This may in part be due to its effect on platelet aggregation. iNOS is upregulated during the inflammatory response. Studies have shown that iNOS derived NO may also have anti-inflammatory characteristics. Id. Collectively, by maintaining vascular tone, promoting angiogenesis, moderating inflammation and inhibiting mast cell degranulation, NO can be viewed as an important molecule for exudate management. Accordingly, exogenously applied nitric oxide may duplicate and supplement the actions of endogenous nitric oxide to reduce the local inflammatory response as well as down regulate the message that the systemic inflammatory response system had been receiving to increase the sending of inflammatory cells. This eventually may lead to a healthy level of exudate production.

FIG. 14 shows that expression of collagenase MRNA is increased as the exposure time to high concentration of gNO (at 200 ppm) increases. This suggests that high concentration of nitric oxide upregulate collagenase that may lead to the enzymatic cleavage of collagen. An independent study by Witte et al (2002) found that MMP-2 activity was also upregulated by NO donors. Witte M B, et al, (2002) *Nitric oxide enhances investigational wound healing in diabetes*, Br J Surg., 89:1594–601. Thus, Applicants believe that NO may upregulate expression of both collagenase (MMP-1) and gelatinase (MMP-2), which may be important in keeping the wound clean from necrotic tissue while not prolonging the inflammatory phase.

Rather than applying exogenous collagenase for enzymatic debridement of necrotic tissue, exposing a wound with necrotic tissue to exogenous NO gas to upregulate endogenous collagenase may be more beneficial. When endogenous collagenase is released by the cell, it automatically releases TIMP's (tissue inhibitor of metalloproteinase). This ensures that the matrix degradation is coordinated and allows the establishment of sharp geographical boundaries of collagenolytic activity and the protection of areas of connective tissue from the activity of the enzyme. In contrast, use of exogenous collagenase material to debride a wound confers no protection to specific areas of the wound as it is active on every cell that comes in contact with it whether or not the effect is desired. The ability of nitric oxide to debride a wound is further supported by the possible inhibition of collagen expression due to high concentration of exogenous nitric oxide applied to the wound, as seen in FIG. 14 (left panel).

Figure 22:
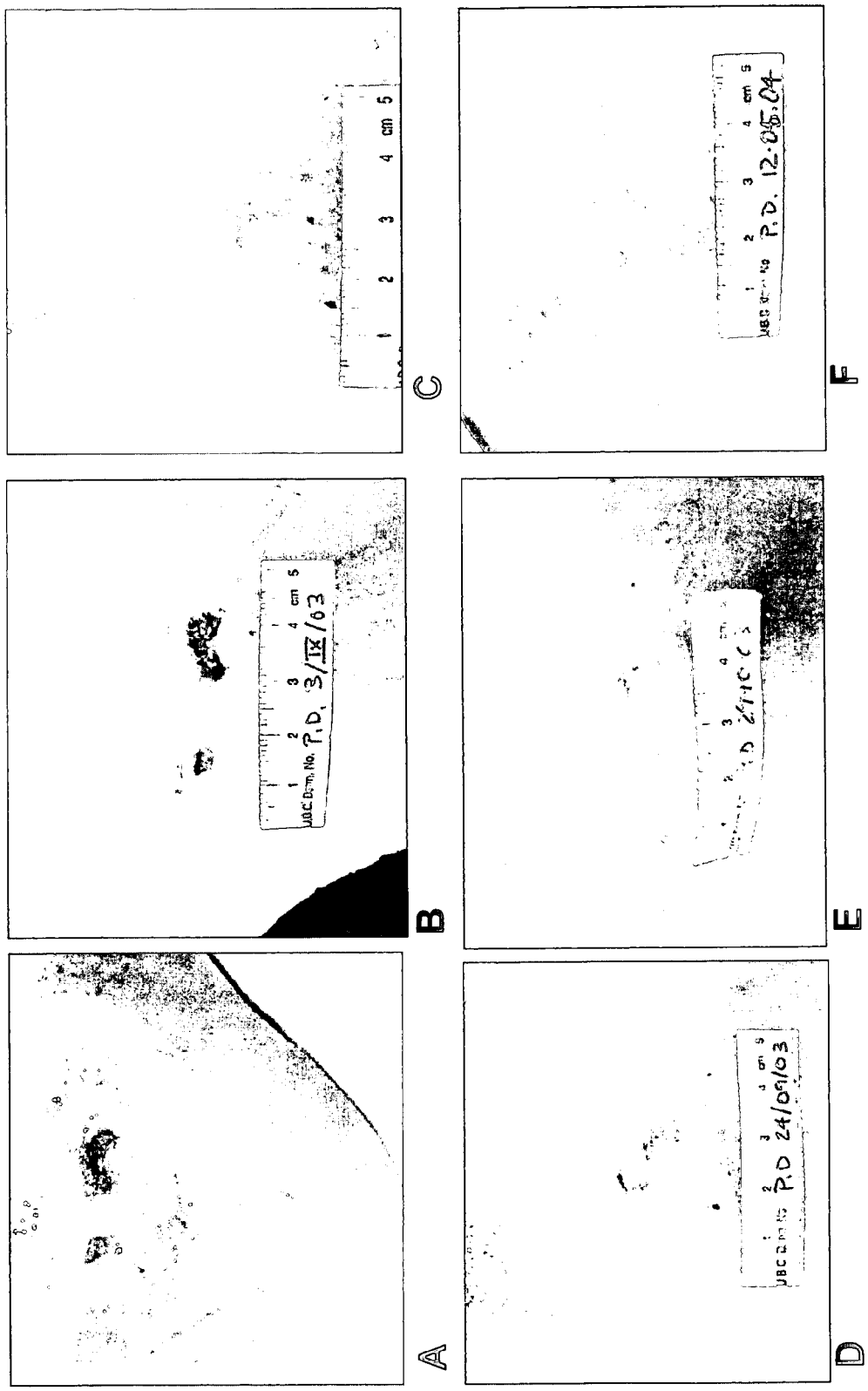
FIG. 22 shows various photographs of a human non-healing leg ulcers at various stages of treatment with nitric oxide gas.

Preferably, after the exposure of the wound to high concentration of nitric oxide gas for a first treatment period (e.g., 5–8 hours per day), the necrotic tissue may be mechanically removed easily and the concentration of nitric oxide gas can be decreased for a second treatment period. The low concentration of nitric oxide gas (e.g., at 5–20 ppm) delivered for the second treatment period may upregulate the expression of collagen mRNA leading to synthesis of new collagen to aid in the closure of the wound. For example, FIG. 22 shows an increased collagen MRNA expression in fibroblast exposed to 5 ppm of NO. The second treatment period may be for a period 7–16 hours per day. Further, the treatment with high and low concentration of nitric oxide gas can be repeated for several days.

For chronic non-healing ulcers on the skin, it is also possible to graft natural skin tissue or synthetically produced skin tissue onto the ulcer after the wound has been prepared. Wound bed preparation may include the reduction of microbial load, debridement, and the management of exudate.

It is believed that the body's natural response to injury is to increase the amount of nitric oxide in order to reduce bacterial count at the injury site, help remove dead cells and then promote healing. The message sent by the injury site has more than just the cells at the injury site producing nitric oxide and this circulates NO around the body in the blood stream. After a few days of this preparation for healing, the body decreases the nitric oxide it produces to a new level that will promote healing. If a wound fails to heal or becomes infected, the body maintains the circulating nitric oxide at a high level and the wound is then caught with a concentration of nitric oxide that may prevent it from healing. It becomes the "Catch 22" of wound healing. Bathing the injury site to high concentration of nitric oxide gas (e.g., 120 ppm to 400 ppm) sends a message to the body that there is enough nitric oxide at the injury site and therefore the body can shut down the extra production by other cells. This enables the local site to heal while it receives the appropriate supraphysiological concentration of nitric oxide gas to inhibit microbial growth.

Additional Safety Studies

In addition to the above study showing no toxicity of in vivo exposure of 200 ppm of nitric oxide gas in an animal model for an open wound, studies to confirm the viability of normal host cells exposed to gNO were performed on fibroblasts, endothelial cells, keratinocytes, alveolar epithelial cells, macrophages, and monocytes, in both flat plate and 3-D growth models for some studies. These experiments looked at viability, proliferation, migration, attachment, expression and tube formation in the appropriate models.

Fibroblast cells obtained from adult patients undergoing elective reconstructive surgery were cultured in Dulbeco's Modified Eagle's Medium (DMEM), supplemented with 10% fetal bovine serum (FBS) and antibiotic-antimycotic preparation and divided into ten 25 cm$^2$ vented culture flasks (COSTAR). Four of these flasks (treated group) were exposed to 20 or 200 ppm humidified gNO inside a specialized NO incubation chamber at 37° C. for 24 and 48 hours. The NO exposure chamber was validated prior to the study to eliminate extraneous variables and ensure optimal conditions for fibroblast cell growth. Another four flasks (control group) were placed inside conventional culture incubator and exposed only to ambient humidified air at 37° C. Two flasks were separately harvested and counted as the number of cells at zero time. Following the treatment, fibroblast cells were harvested and evaluated for morphology, cell count, capacity to proliferate and medium pH. The results from these experiments show that exposure to around 200 ppm of gNO did not have harmful effects on the fibroblast.

FIG. 15 shows morphology of fibroblast cells from the viability study, where cultured human fibroblast cells were exposed to various gNO concentrations less than 200 ppm continuously for 48 hours. Morphological appearance and attachment capacity of control and treated dermal fibroblasts cells following 48 hours period were quite comparable. Cells under gNO appeared healthy and attached to the culture plates. No toxic effect due to exposure to gNO was observed.

Figure 16:
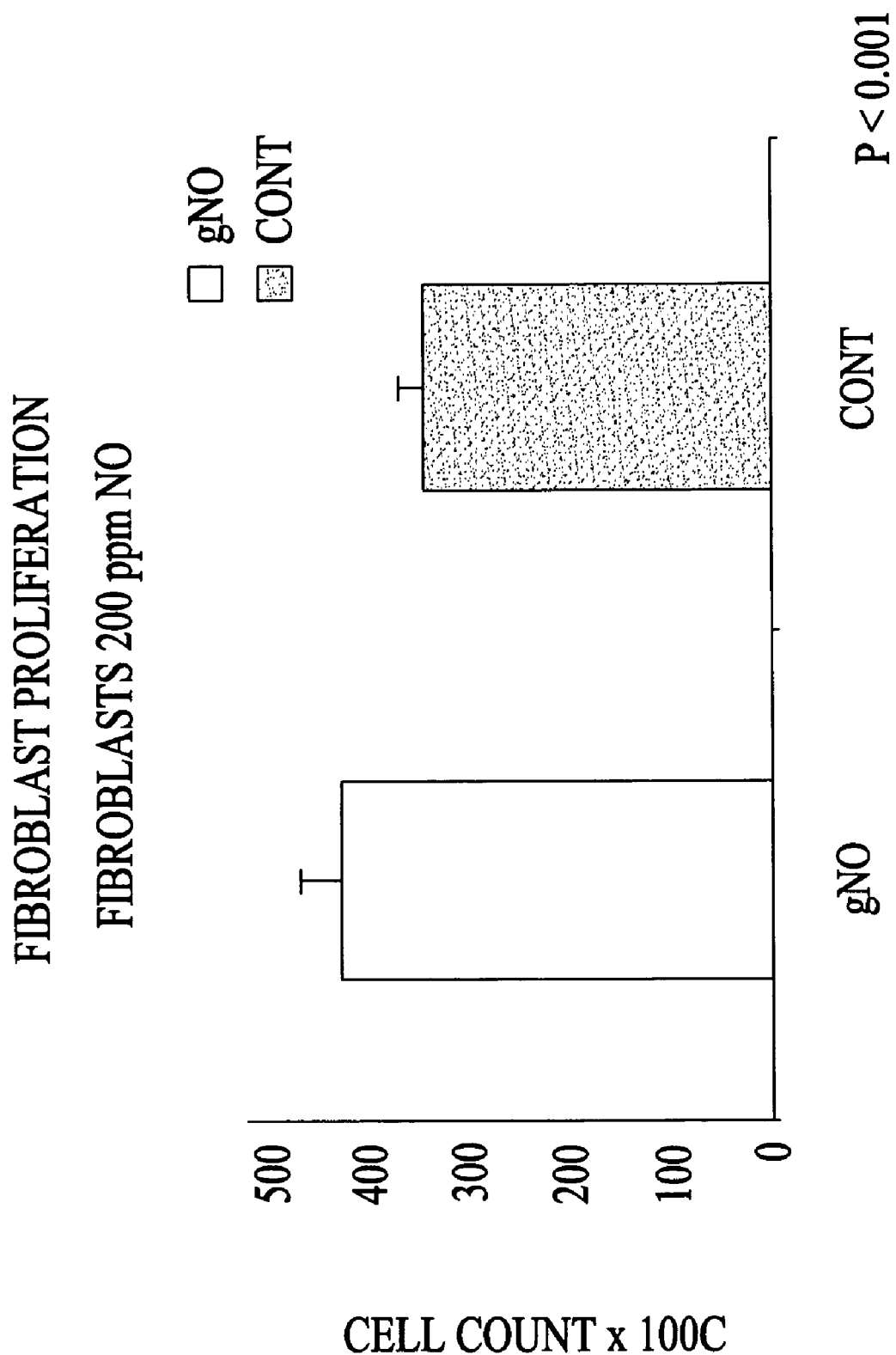
FIG. 16 illustrates increase in fibroblast cell proliferation following exposure to 200 ppm of NO in comparison with control.

FIG. 16 shows that, in addition to a lack of toxicity to fibroblast cells, exposure to 200 ppm NO may also have positive effect of increasing proliferation of fibroblast cells that may further aid in the wound healing process.

Figure 17:
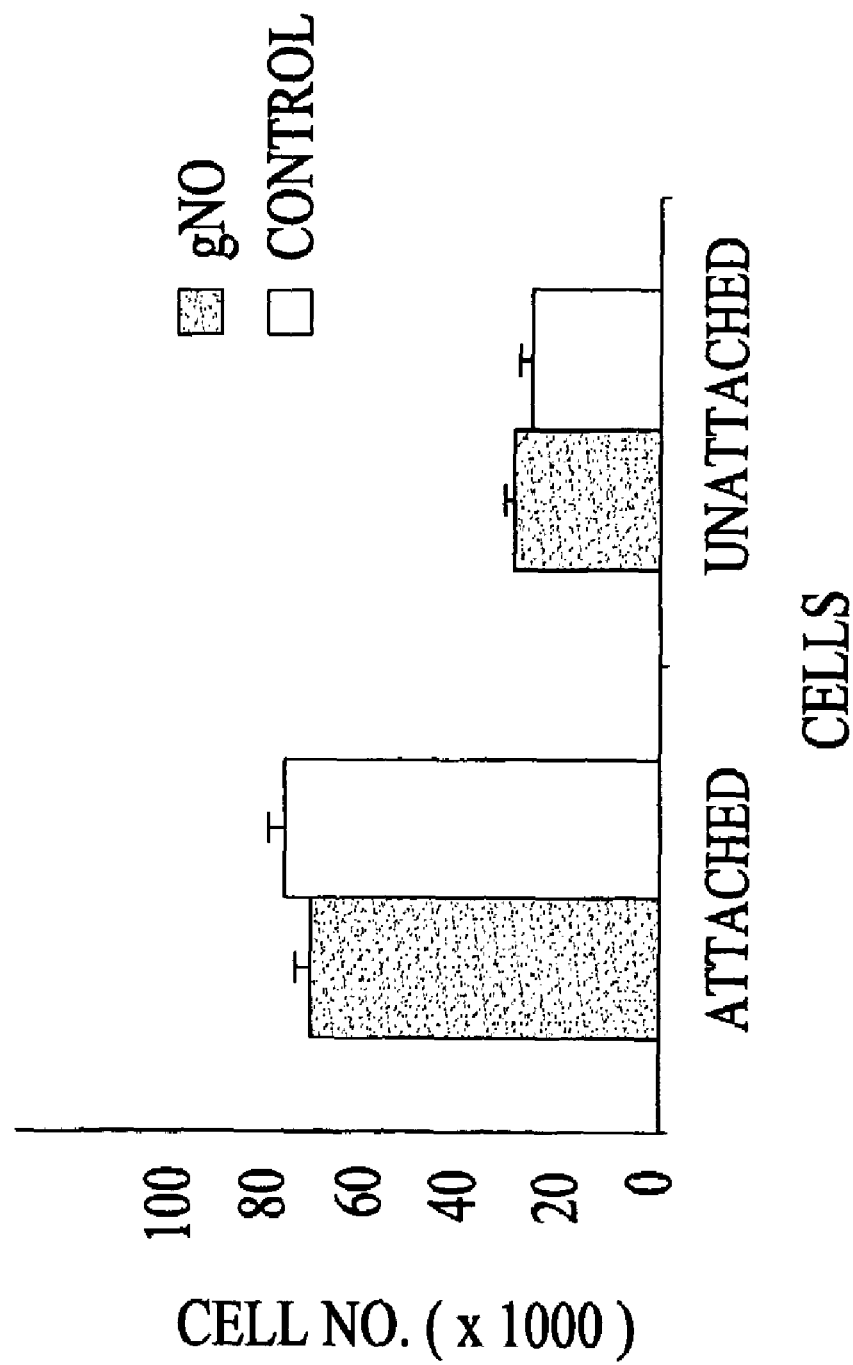
FIG. 17 illustrates cell attachment capacity of human fibroblasts following exposure to 160 ppm of gNO.

FIG. 17 shows results from cell attachment capacity from the fibroblast cells exposed to 160 ppm of gNO. Capability of cells to reattach to the culture plates within a specified time limit is commonly used as an indication of viability of cells in culture. Both the control and treated groups show a 70% attachment capacity within 1 hour of culturing. This result in conjunction with cell morphology and count support the safety of gNO therapy for topical applications on mammalian skin tissue at least at a range between 100 to 200 ppm of gNO.

Figure 18:
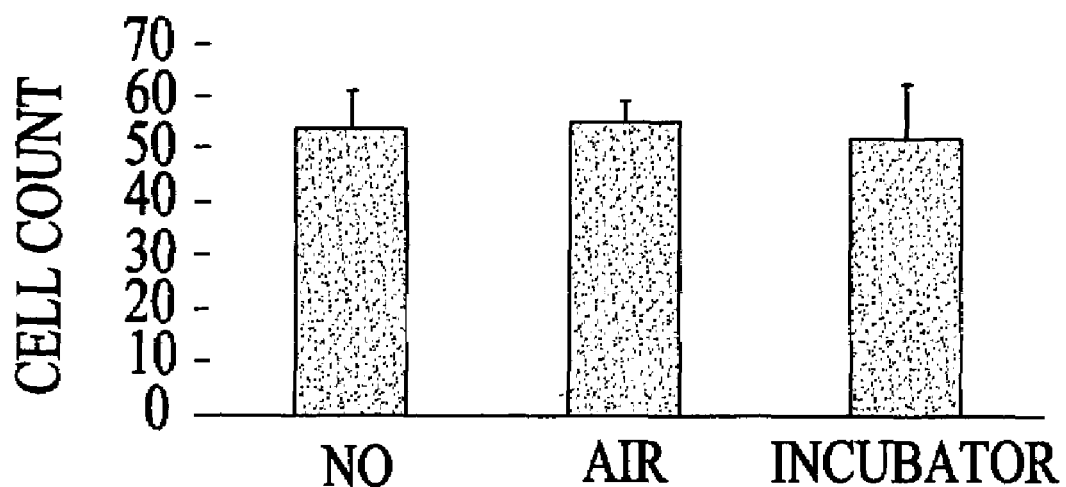
FIG. 18 shows the results of fibroblasts grown in a 3D matrix and exposed to 200 ppm NO for 8 hours per day for 3 days compared with control cells in air or conventional incubator.

FIG. 18 shows the amount of migration of fibroblasts grown in a 3D matrix and exposed to 200 ppm NO for 8 hours per day for 3 days compared with control cells in air or conventional incubator. As seen from these results, NO does not appear to affect (or more specifically does not interfere with) the migration of these fibroblasts under these conditions.

Figure 19:
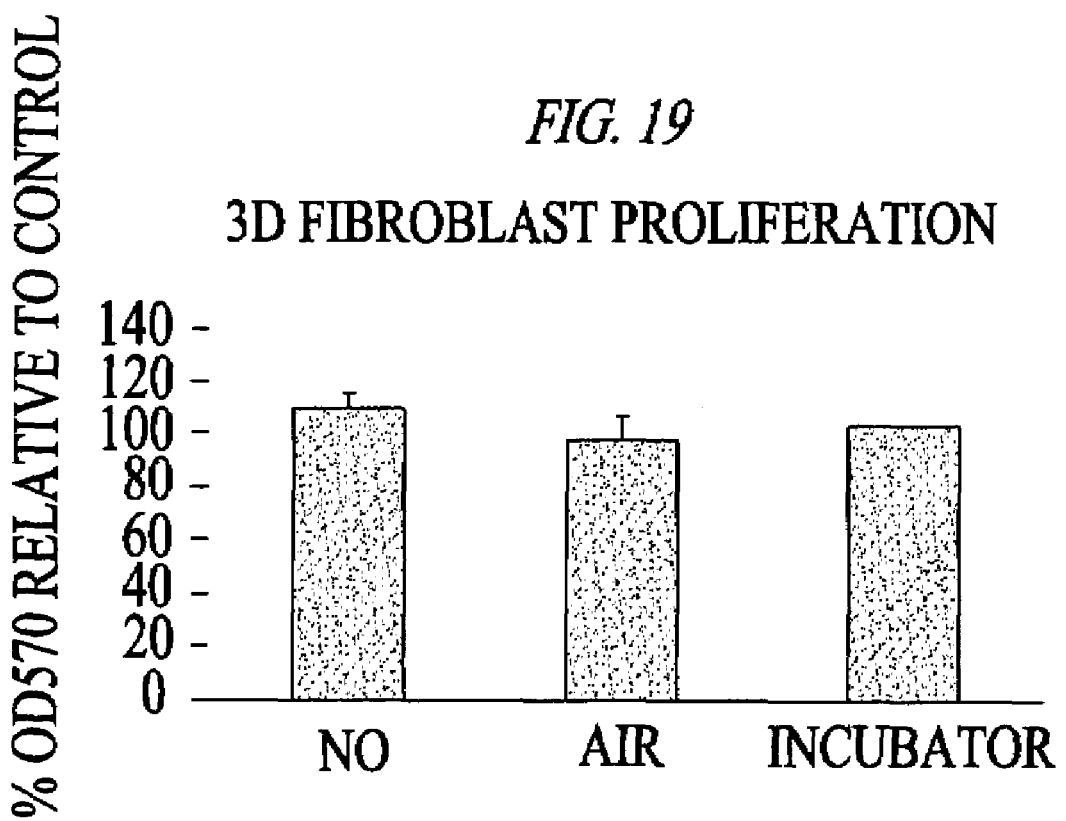
FIG. 19 shows the amount of proliferation of fibroblasts grown in a 3D matrix and exposed to 200 ppm NO for 8 hours per day for 3 days compared with control cells in air or conventional incubator.

FIG. 19 shows the amount of proliferation of fibroblasts grown in a 3D matrix and exposed to 200 ppm NO for 8 hours per day for 3 days compared with control cells in air or conventional incubator. Again, NO does not appear to interfere with the proliferation of fibroblasts under these conditions.

Figure 20:
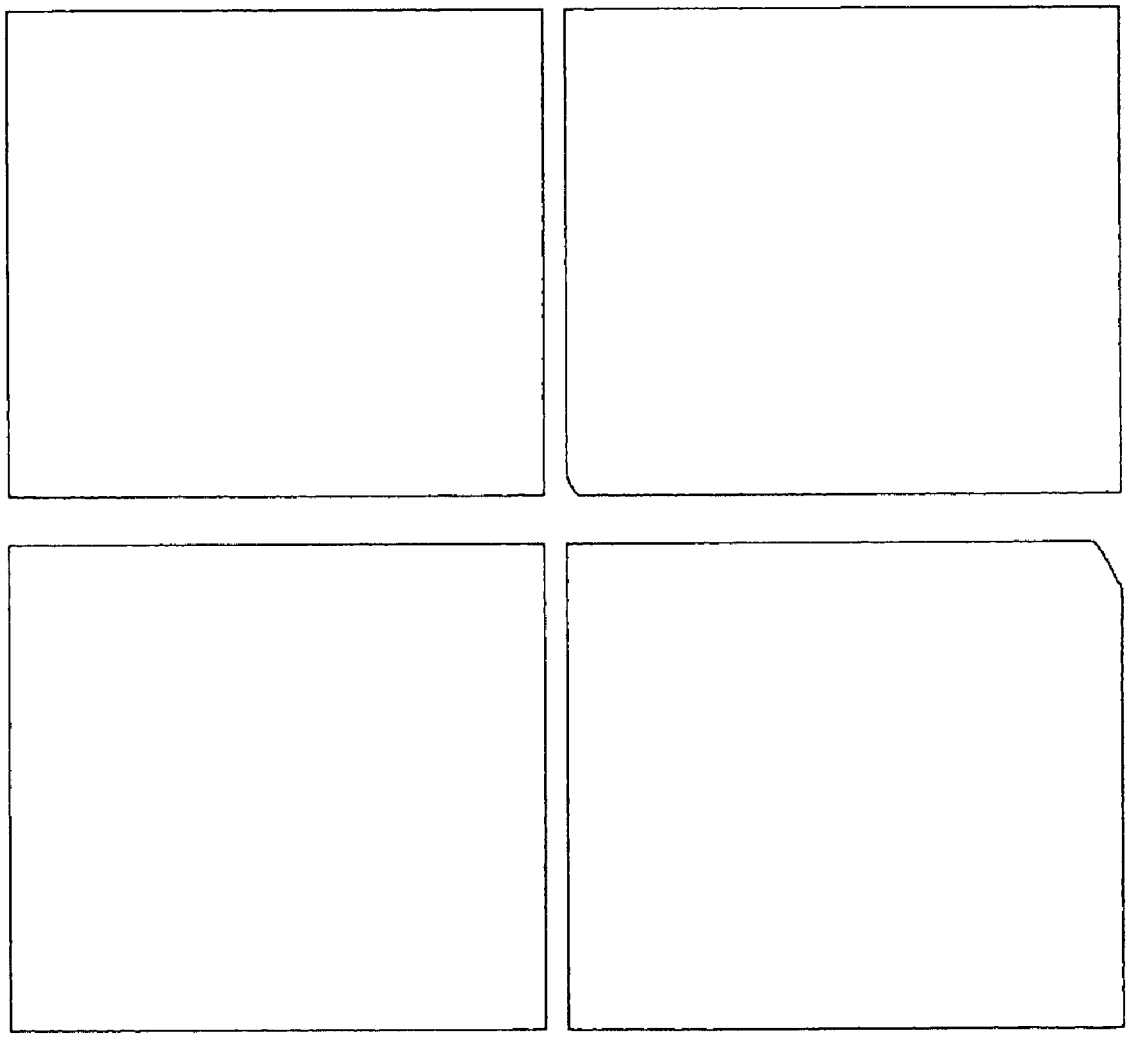
FIG. 20 shows the amount of tube formation in human endothelial cells grown in matrigel and exposed to air (top panels) or 200 ppm NO (bottom panels) for 24 hours. Left panels at 8 hours of exposure. Right panels at 24 hours of exposure.
Figure 21:
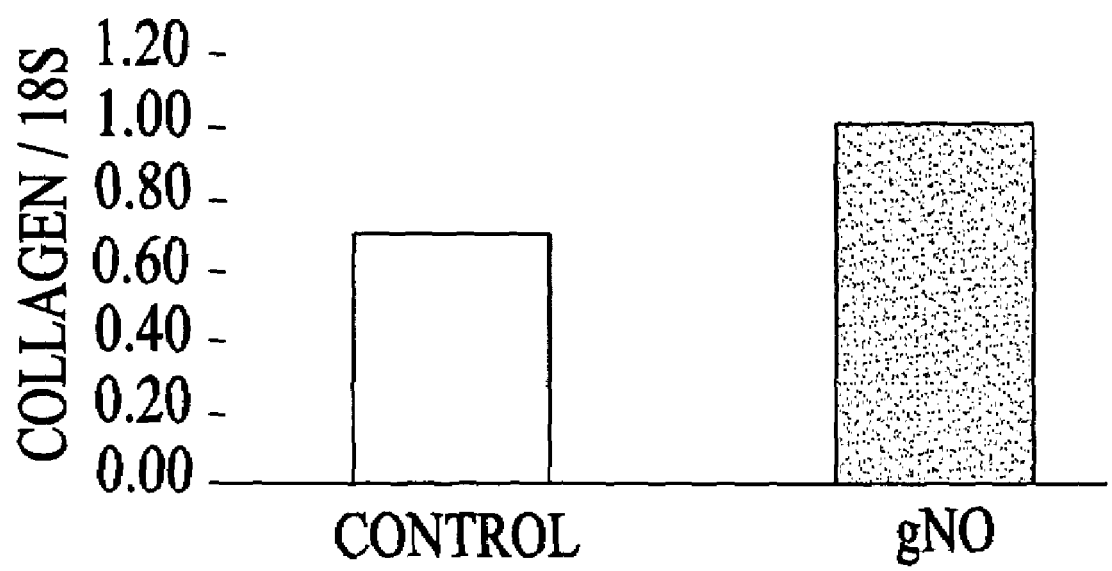
FIG. 21 shows an increased collagen MRNA expression in fibroblast exposed to 5 ppm of NO.

FIG. 20 shows the tube formation in human endothelial cells grown in matrigel and exposed to air (top panels) or 200 ppm NO (bottom panels) for 8 hours (left panels) or 24 hours (right panels). Again, no significant difference between exposure to air and 200 ppm can be discerned.

Human Case Study

This case study involved a 55-year-old man with a 30 year history of severe venous disease, both deep and superficial, related to deep vein thrombophlebitis. Initially, while in his twenties, the patient developed bilateral non-healing venous leg ulcers that were surgically treated. The surgical sites healed but the ulcers continued to recur. Initially, the patient presented with a small ulcer located just below the medial malleolus of the left ankle. Although not increasing in size, this ulcer did not completely heal with two years of standard of care therapy.

Most of the time the wound base was covered with a biofilm—a tenacious, yellow-colored, gel-like material. Edema control was maintained by using graduated compression stockings. Antimicrobial dressings were tried including Manuka Honey, a starch iodine preparation (Iodosorb, Smith & Nephew, Largo, Fla., USA), and colloidal silver (Aquacel AG, ConvaTec, Princeton, N.J., USA). His wound was frequently debrided in order to physically remove the biofilm. This was generally ineffective as the biofilm was frequently noted to be present again at the next visit. Twenty percent benzyol peroxide lotion was applied every few days in order to trigger the development of granulation tissue; however, this was ineffective as well. At times there would be improvement as the ulcer would appear to become covered with new skin only to break down weeks later. This poor progress to complete closure was noted despite wound care that addressed proper moisture balance, wound bed preparation, and treatment of the underlying disease.

This failure of his wound to close had a significant impact on quality of life for this patient. He made clinic office visits at least once a month for the entire two years. The cost of the treatment, including the surgeons time and treatment materials (several thousand dollars), put pressure on the health care system as well as on the patient, with him having to travel several hours each visit for treatment. As previous treatments proved ineffective, the patient was invited to participate in this experimental study. Following a discussion of the experimental therapy and potential risks, an informed consent was obtained.

The patient was seen at the clinic where the wound was assessed and photographed (FIG. 22). The treatment regimen was explained and the use of the CidaNOx Delivery System and boot was demonstrated. Arrangements were made to meet at the patient's home the following day to set up the equipment and for him to have a repeat training on the use of the treatment system. Training included use of the system as well as safety information on using the gas equipment.

Nitric oxide gas (ViaNOx-H, VIASYS Healthcare, Yorba Linda, Calif., USA) was applied to the lower extremity with use of a gas-diluting delivery system (CidaNOx Delivery System) designed specifically for the study (PulmoNOx Medical Inc., Edmonton, Alberta, Canada). This CidaNOx delivery system contains an internal air pump for dilution of the gNO and a flow control circuit to dilute the 800 parts per million (ppm) in the NO source cylinder down to the therapeutic level of 200 ppm. The total flow from the system was 1.0 L/min and included one-quarter of a liter per minute (250 ml/min) flow of gNO. Several internal pressure sensors assure the dilution flow is operational and monitor the system. The flow of nitric oxide was limited to 250 ml/min by a mechanically set pressure regulator and a mechanical flowmeter that have no external controls that could be changed by the patient. The concentration of nitric oxide delivered was assured by measurement of the CidaNOx output with a calibrated nitric oxide analyzer (AeroNOx, Pulmonox Medical Inc.) that is approved for monitoring inhaled NO in human patients.

The 200 ppm gNO from the CidaNOx Delivery System flowed out to a single patient use plastic boot that covered the patient's lower extremity. The boot had an inflatable cuff near the top that provided a low-pressure seal. A secondary air outlet from the CidaNOx unit managed the inflation of the cuff. The patient connected the pump outlet to the cuff connector until it was inflated and then the connector was sealed closed with the provided clamp. The gNO flow was then connected to the inlet connector near the toe of the boot and the return line to the connector near the top of the boot. The return line passed through the CidaNOx unit and then out through a scavenger consisting of charcoal and potassium permanganate that absorbs the nitrogen oxides. The CidaNOx Delivery System had two toggle positions, one for delivery of gNO and the other for delivery of air only. At the end of the treatment period, the patient switched the delivery flow to air only so as to clear the boot of remaining gNO before taking the boot off.

The patient was instructed to continue wearing supportive stockings and to use a hydrofiber dressing (Aquacel, Convatec) on the wound when not receiving gNO treatment. During the gNO treatment, he removed the supportive stocking and replaced the Aquacel dressing with a porous, low adherence dressing (ETE, Molnlycke Health Care, Sweden), which had previously been shown to allow the diffusion of gNO through it (data not shown).

To explore the potential for wound bed preparation and accelerated wound healing from prolonged use, treatment regimen beyond three days was chosen and which was stopped at 14 days to evaluate the short-term effects and explore the possibility that the short-term effects would improve the longer-term outcome. The patient was encouraged to wear the gNO boot as often as possible during each 24-hour period. As the patient worked during the day, it was decided that it would be most practical to wear the boot and receive the gNO treatments only while in bed at night. The patient recorded the date, time, and duration of each treatment period on a data sheet, and any significant observations related to the wound, treatment, or equipment. The wound size (cm²) was measured using digital photography and densitometry technique (Scion Image –4.02, Scion Corp., Frederick Md., USA).

The patient self-administered the treatment for 14 consecutive nights. The nocturnal treatment duration varied from 6.5 to 9.75 hour per treatment. The cumulative wound exposure to 200 ppm gNO during the 14 treatment periods was 105.25 hour. The wound was assessed and photographed on day 0 (FIG. 22A, pretreatment), day 3 (FIG. 22B, following accumulative 24 hour of gNO exposure), and day 14 (FIG. 22C). The wound was also assessed and photographed ten days following the completion of the 14-day treatment (FIG. 22D) and in the 6th and 26th week following the completion of the treatment (FIGS. 22E and 22F, respectively).

During the active treatment period, the subject was assessed with respect to the use of the CidaNOx system. The subject found the system easy to use in a fixed location, found the application of the bag comfortable, and never reported any pain associated with its use. He suffered no bleeding episodes. FIG. 23A shows the initial presentation of the ulcer prior to use of the gNO. The wound base was covered by a biofilm and there was little healthy granulation tissue present and there was no evidence of new skin growth from the edges. The wound was malodorous.

Figure 23:
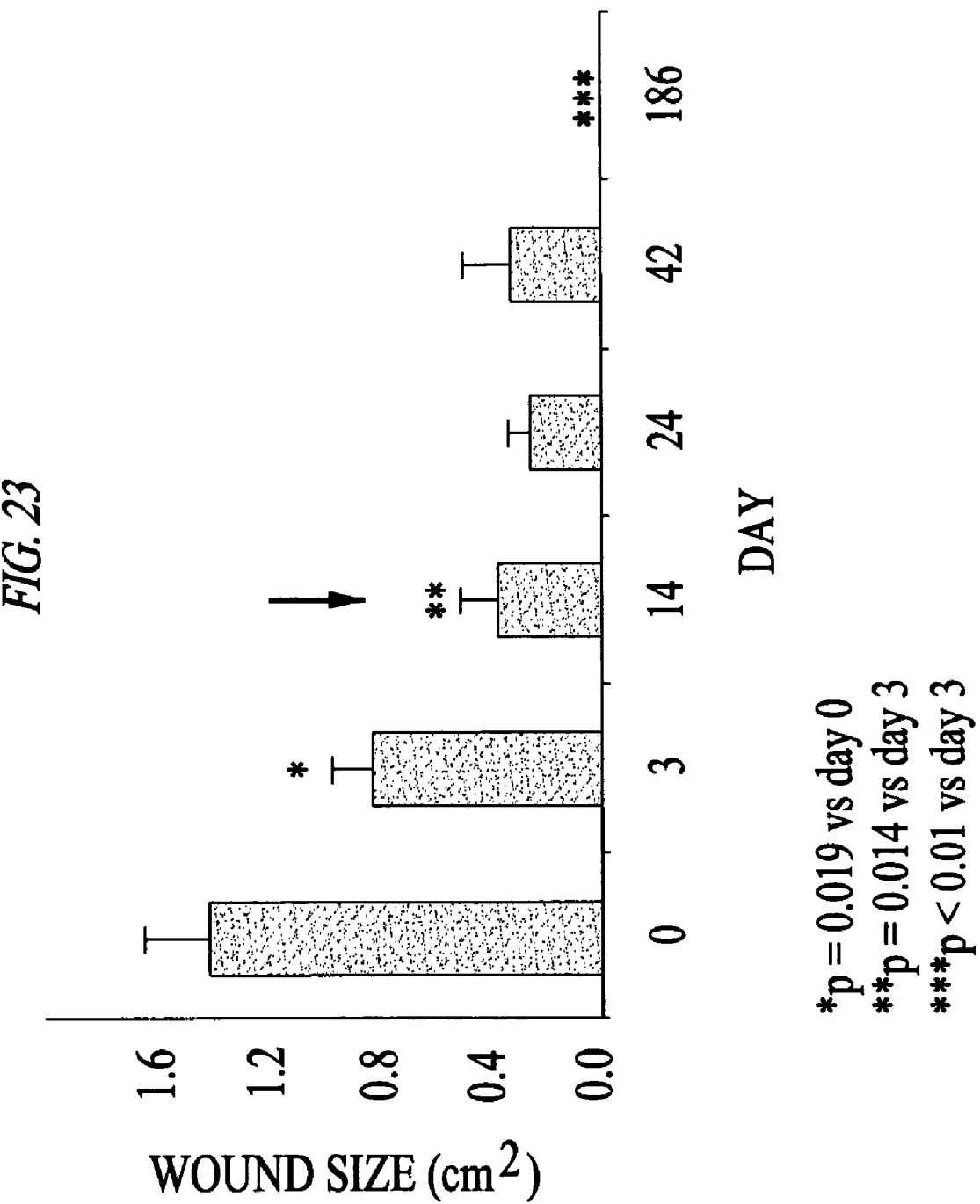
FIG. 23 shows the reduction in wound size in the human non-healing ulcer of FIG. 23 following nitric oxide gas treatment. Significant decrease in area was observed following 3 and 14 days of gNO application to the wound (*$p=0.019$ vs. day 0; $p=0.014$ vs. day 3). Wound status did not deteriorate after removal of treatment (arrow, day 14). Wound was completely healed following 26 weeks (186 days; *$p<0.01$ vs. day 3). Values are means and standard deviations.

After 24 hours of NO exposure (3 days at 8 hours day), for the first time there was healthy granulation tissue noted in the ulcer base. There was also early evidence of new skin growth from the edges observed. The malodorous odor was also absent. Concomitantly, there was less biofilm present (FIG. 22B). At 14 days of therapy (FIG. 22C) the ulcer clearly had diminished in size. By then it had almost completely epithelialized. Significant wound size reduction was observed as early as day 3 of gNO treatment (p=0.014), with approximately 75% reduction in wound area by the end of gNO therapy at day 14 (FIG. 23). The wound was further assessed 10 days after cessation of gNO treatment (FIG. 22D). There did not appear to be any deterioration of the wound during this time, although the ulcer was judged to be incompletely healed. No significant deterioration in wound size was observed compared to the last day of gNO treatment (FIG. 23). Six weeks later the wound was judged to be about 90% healed with no deterioration in wound size or epithelialization (FIG. 22E and FIG. 23). At 26 weeks post NO discontinuation, the ulcer was noted to be completely healed and reepithelialized (FIG. 22F). Over the entire post-treatment time, there were no changes to the dressing regimen and no other anti-microbials or antibiotics were used.

The average time for ulcers that result from venous stasis disease to heal under optimal care ranges from 12 to 16 weeks. Our patient, who had a nonresponsive ulcer for more than two years, exhibited a positive response to a brief exposure to gaseous nitric oxide. His wound decreased in size, a granular base was established, and the malodorous smell was eradicated during this two-week period. Further studies and randomized controlled trials will be able to answer whether a longer exposure or a different concentration, once the biofilm was eliminated, would have made a difference in the closure of the lesions.

While embodiments of the present invention have been shown and described, various modifications may be made without departing from the scope of the invention. For example, the types of tissue that may have wounds to be treated using the methods described herein may include, without limitation, the skin, muscle, tendon, ligament, mucosa, bone, cartilage, cornea, and exposed internal organs. The tissue may be damaged by surgical incisions, trauma (mechanical, chemical, viral, bacterial, or thermal in nature), or other endogenous pathological processes. The invention, therefore, should not be limited, except to the following claims, and their equivalents.

What is claimed:

1. A method to promote healing of a wound of a subject, the method comprising the steps of:
   providing a flow-controlled source of nitric oxide gas;
   exposing the wound to a high concentration of exogenous nitric oxide gas for a treatment period without inducing toxicity to the subject or the healthy cells surrounding the wound; and
   exposing the wound to a decreased concentration of exogenous nitric oxide gas for a second treatment period sufficient to increase the expression of collagen MRNA.

2. The method of claim 1, further comprising the step of monitoring the concentrations of nitric oxide gas.

3. The method of claim 2, wherein the decreased concentration of nitric oxide gas is about 5 ppm.

4. The method of claim 2, wherein the treatment period is about 7 hours and the second treatment period is at least about 7 hours.

5. The method of claim 1, further comprising the step of monitoring of the levels of collagenase produced by cells surrounding the wound.

6. The method of claim 1, further comprising the step of monitoring the levels of collagen produced by cells surrounding the wound.

7. The method of claim 1, further comprising the step of removing of excess exudate from the wound.

8. The method of claim 1, wherein the high concentration of nitric oxide gas is greater than about 200 ppm.

9. The method of claim 8, wherein the high concentration of nitric oxide gas is about 200 ppm to 400 ppm.

10. The method of claim 1, wherein the treatment period is at least about 7 hours.

11. The method of claim 10, wherein the exposure to the high concentration of nitric oxide gas in the first treatment period is continuous.

12. A method of reducing scarring in a healing process of a wound, the method comprising the steps of:
   providing a flow-controlled source of nitric oxide gas;
   exposing the wound to a high concentration of exogenous nitric oxide gas for a treatment period without inducing toxicity to the subject or to healthy cells surrounding the wound,
   exposing the wound to a decreased concentration of exogenous nitric oxide gas for a second treatment period sufficient to increase the expression of collagen mRNA; and
   exposing the wound to a third concentration of exogenous nitric oxide gas for a third treatment period, wherein the third concentration is between the high concentration and the decreased concentration.

13. The method of claim 12, wherein the high concentration ranges from about 200 ppm to 400 ppm, the decreased concentration ranges from about 5 ppm to 20 ppm, and the third concentration ranges from about 20 ppm to 200 ppm.

14. The method of claim 12 wherein the first treatment period is at least seven hours in a day, the second treatment period ranges from 5–12 hours a day, and the third treatment period ranges from about 5–12 hours a day.

15. The method of claim 14 wherein the first treatment period, the second treatment period, and the third treatment period are repeated for multiple days.

* * * * *